US012173084B2

(12) United States Patent
Arur

(10) Patent No.: US 12,173,084 B2
(45) Date of Patent: Dec. 24, 2024

(54) PHOSPHORYLATED DICER ANTIBODY AND METHODS OF USE THEREOF

(71) Applicant: Board of Regents, The University of Texas System, Austin, TX (US)

(72) Inventor: Swathi Arur, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 680 days.

(21) Appl. No.: 17/416,198

(22) PCT Filed: Dec. 23, 2019

(86) PCT No.: PCT/US2019/068373

§ 371 (c)(1),
(2) Date: Jun. 18, 2021

(87) PCT Pub. No.: WO2020/132684

PCT Pub. Date: Jun. 25, 2020

(65) Prior Publication Data

US 2022/0056155 A1 Feb. 24, 2022

Related U.S. Application Data

(60) Provisional application No. 62/812,743, filed on Mar. 1, 2019, provisional application No. 62/784,032, filed on Dec. 21, 2018.

(51) Int. Cl.

| | |
|---|---|
| ***C07K 16/00*** | (2006.01) |
| ***A01K 67/0278*** | (2024.01) |
| ***A61K 39/395*** | (2006.01) |
| ***A61P 35/00*** | (2006.01) |
| ***C07K 16/44*** | (2006.01) |
| ***G01N 33/574*** | (2006.01) |

(52) U.S. Cl.

CPC .......... *C07K 16/44* (2013.01); *A01K 67/0278* (2013.01); *A61P 35/00* (2018.01); *G01N 33/57407* (2013.01); *A01K 2217/072* (2013.01); *A01K 2227/105* (2013.01); *A01K 2267/0331* (2013.01)

(58) Field of Classification Search

CPC .............. A61P 35/00; G01N 33/57407; A01K 2267/0331

See application file for complete search history.

(56) References Cited

U.S. PATENT DOCUMENTS

| | | | |
|---|---|---|---|
| 2011/0300156 | A1 | 12/2011 | Verploegen et al. |
| 2013/0203079 | A1 | 8/2013 | Goodman et al. |
| 2014/0199301 | A1 | 7/2014 | Erdag et al. |
| 2016/0355599 | A1 | 12/2016 | Sagert et al. |

OTHER PUBLICATIONS

Paul, Fundamental Immunology, 3rd Edition, 1993, pp. 292-295, under the heading Fv Structure and Diversity in Three Dimensions.*

Aryal et al., "Constitutive Dicer1 phosphorylation accelerates metabolism and aging in vivo," *PNAS*, 116(3):960-969, 2018.

Aryal et al., "Dicer1 Phosphomimetic Promotes Tumor Progression and Dissemination," *Cancer Research*, 79(10):2662-2668, 2019.

Aryal et al., Loss of digestive organ expansion factor (Diexf) reveals an essential role during murine embryonic development that is independent of p53. Oncotarget 8(61):103996-104006, 2017.

Aryal, "Phosphorylation impairs DICER1 function to accelerate aging and tumorigenesis in vivo," *UT GSBS Dissertations and Theses*, 838, 2018.

Burger et al., "Nuclear phosphorylated Dicer processes double-stranded RNA in response to DNA damage," *The Journal of Cell Biology*, 216(8):2373-2389, 2017.

Burger et al., "Nuclear-re-localization of Dicer in primary mouse embryonic fibroblast nuclei following DNA damage," *PLoS Genetics*, 14(2):1-18, 2018.

Drake et al., "A requirement for ERK-dependent dicer phosphorylation in coordinating oocyte-to-embryo transition in *C. elegans,*" *Developmental Cell*, 31:614-628, 2014.

Extended European Search Report issued in European Application No. 19900790.7, mailed Dec. 9, 2022.

Hill et al., DICER1 mutations in familial pleuropulmonary blastoma. Science, 325(5943): p. 965, 2009.

Kumar et al., Dicer1 functions as a haploinsufficient tumor suppressor. Genes Dev, 23(23): p. 2700-4, 2009.

Mudhasani et al., Loss of miRNA biogenesis induces p19Arf-p53 signaling and senescence in primary cells. J Cell Biol 181(7):1055-1063, 2008.

Nicholson et al., "Molecular characterization of a mouse cDNA encoding Dicer, a ribonuclease III ortholog involved in RNA interference," *Mammalian Genome*, 13(2):67-83, 2002.

PCT International Preliminary Report on Patentability issued in International Application No. PCT/US2019/068373, mailed Jul. 1, 2021.

PCT International Search Report and Written Opinion issued in International Application No. PCT/US2019/068373, mailed Jun. 11, 2020.

Pugh et al., Exome sequencing of pleuropulmonary blastoma reveals frequent biallelic loss of TP53 and two hits in DICER1 resulting in retention of 5p-derived miRNA hairpin loop sequences. Oncogene, 33(45): p. 5295-302, 2014.

Rakheja et al., Somatic mutations in DROSHA and DICER1 impair microRNA biogenesis through distinct mechanisms in Wilms tumours. Nat Commun, 2: p. 4802, 2014.

Reyes-Castro et al., "ERK dependent DICER1 phophorylation promotes open chromatin state and lineage plasticity to mediate tumor progression," bioRxiv preprint, 2022.

(Continued)

*Primary Examiner* — Mark Halvorson

(74) *Attorney, Agent, or Firm* — Parker Highlander PLLC

(57) ABSTRACT

Provided herein are phosphorylated Dicer 1 (pDicer1) antibodies, including those that selectively bind Serine 1728 and/or Serine 1852. Further provided herein are methods of treating cancer by administering the pDicer1 antibodies alone or in combination with other therapies.

17 Claims, 22 Drawing Sheets

Specification includes a Sequence Listing.

(56) References Cited

OTHER PUBLICATIONS

Strausberg et al., "Generation and initial analysis of more than 15,000 full-length human and mouse cDNA sequences," *Proceedings of the National Academy of Sciences of the USA*, 99(26):16899-16906, 2002.

* cited by examiner

| Tumor Type | KRas+/LA1 n = 17 | KRas+/LA1; Dicer+/2SD n = 24 |
|---|---|---|
| Lung adenocarcinoma | 16 | 21 (1*) |
| Lymphoma | - | 5 (5*) |
| Histiocytic sarcoma | - | 6 (6*) |
| Hepatocellular carcinoma | - | 1 |
| Mesothelioma | - | 1 |
| Endothelial cell Tumor | - | 1 |
| Hemangiosarcoma | - | 1 |
| Hemangioma | - | 1 |
| Mice with >1 Tumor Types | - | 14 |
| Total mice with tumors | 16 | 24 |

*dissemination/metastasis

| Tumor Type | $p53^{+/-}$ n = 12 | $p53^{+/-}$; $Dicer^{+/2SD}$ n = 21 |
|---|---|---|
| **Sarcoma** | | |
| Osteosarcoma | 2 | 6 |
| Histiocytic sarcoma | - | 2 (2*) |
| Hemangiosarcoma | - | 1 |
| Unspecified | - | 1 |
| **Lymphoma** | 1(1*) | 6 (3*) |
| **Carcinoma** | | |
| Lung adenocarcinoma | - | 1 |
| Testicular carcinoma | - | 1 (1*) |
| Hepatocellular carcinoma | - | 1 |
| Unspecified | - | 1 |
| Mice with >1 Tumor Types | - | 5 |
| Total mice with tumors | 3 | 15 |

*dissemination/metastasis

| Allele | $Dicer^{S1712D}$ | $Dicer^{\Delta 1712}$ | $Dicer^{-}$ | $Dicer^{S1836D}$ | $Dicer^{2SD}$ |
| --- | --- | --- | --- | --- | --- |
| Mutation | Ser1712Asp | Ser1712Deletion | Ser1712-4aa-STOP | Ser1836Asp | Ser1712, 1836Asp |
| WT | 17 (21) | 21 (17) | 8 (7) | 28 (26) | 34 (29) |
| Het | 48 (43) | 35 (34) | 20 (14) | 48 (52) | 73 (58) |
| Homo | 20 (21) | 12 (17) | 0 (7) | 11 (26) | 8 (29) |
| P-Value | 0.440 | 0.300 | 0.008 | 0.003 | <0.001 |

| Genotype | Sex | # Mating pairs | # Litters | Average litter size |
|---|---|---|---|---|
| $Dicer^{S1712D/S1712D}$ | Male | 5 | 5 | 8.4 |
| $Dicer^{S1712D/S1712D}$ | Female | 5 | 5 | 7.8 |
| $Dicer^{\Delta1712/\Delta1712}$ | Male | 3 | 3 | 8.7 |
| $Dicer^{\Delta1712/\Delta1712}$ | Female | 4 | 4 | 8.0 |
| $Dicer^{S1836D/S1836D}$ | Male | 11 | 0 | 0 |
| $Dicer^{S1836D/S1836D}$ | Female | 9 | 0 | 0 |
| $Dicer^{2SD/2SD}$ | Male | 11 | 0 | 0 |
| $Dicer^{2SD/2SD}$ | Female | 13 | 0 | 0 |

FIG. 5E

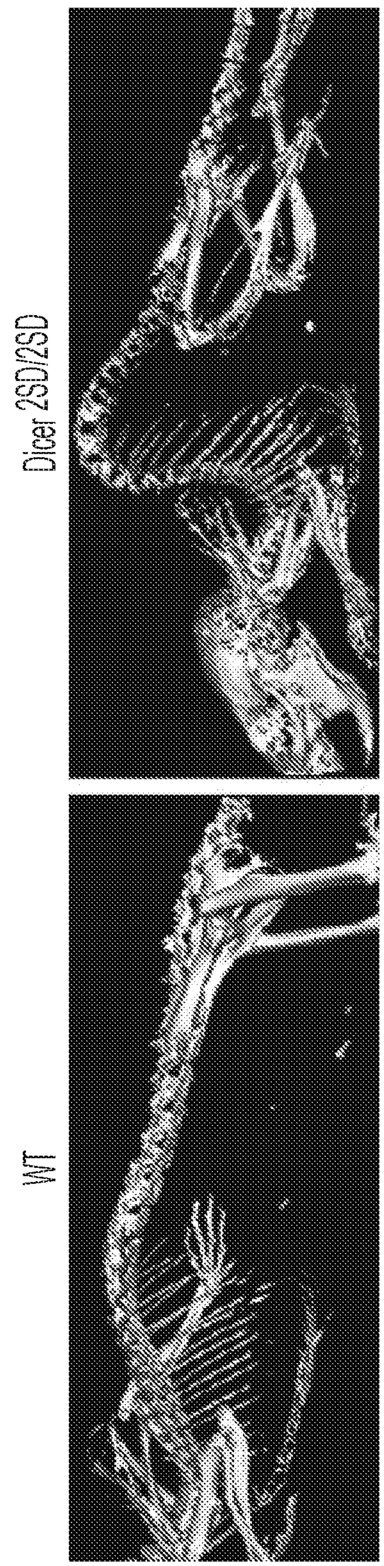
FIG. 6A
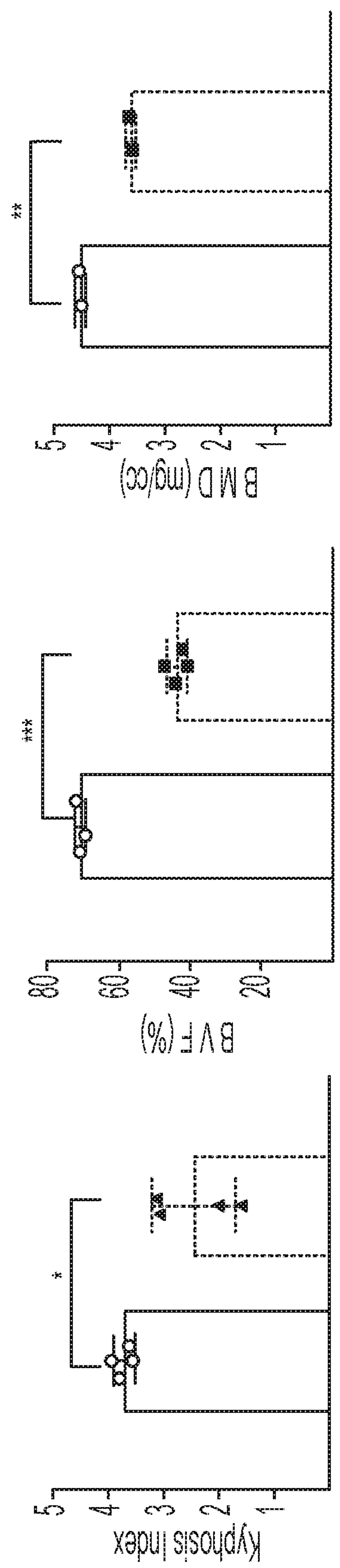
FIG. 6B
FIG. 6C
FIG. 6D

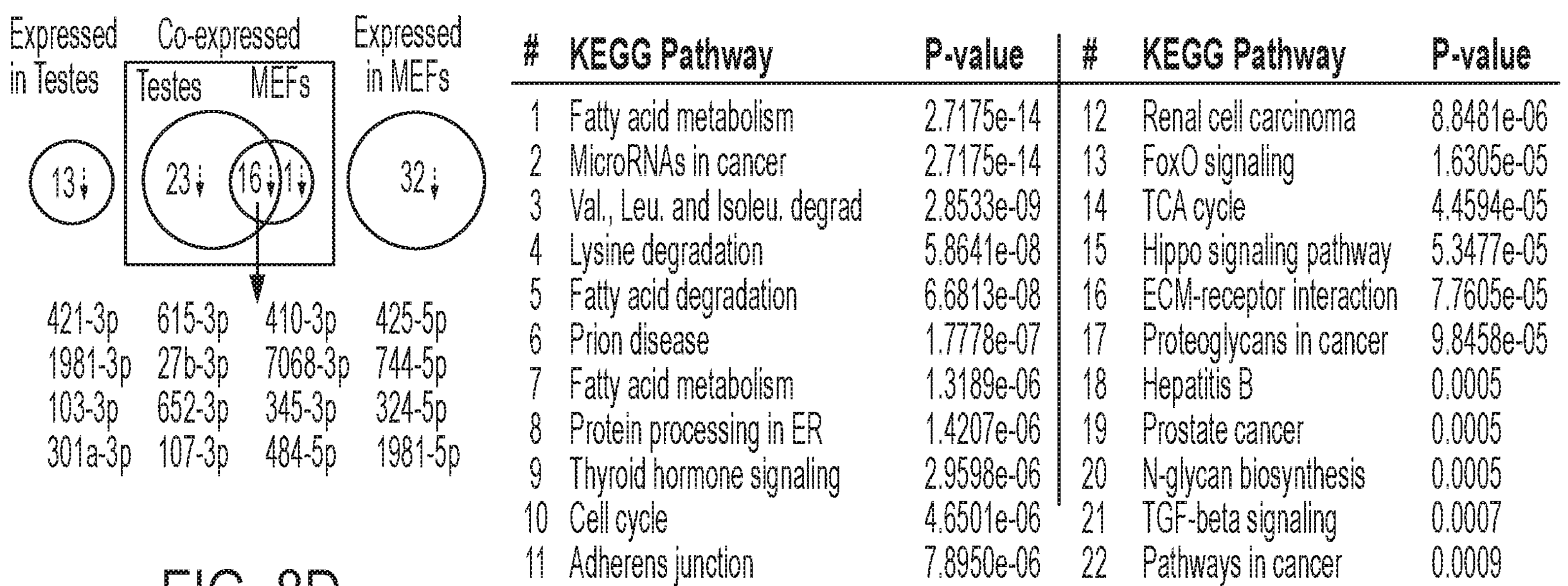

FIG. 8D

| # | KEGG Pathway | P-value | # | KEGG Pathway | P-value |
|---|---|---|---|---|---|
| 1 | Fatty acid metabolism | 2.7175e-14 | 12 | Renal cell carcinoma | 8.8481e-06 |
| 2 | MicroRNAs in cancer | 2.7175e-14 | 13 | FoxO signaling | 1.6305e-05 |
| 3 | Val., Leu. and Isoleu. degrad | 2.8533e-09 | 14 | TCA cycle | 4.4594e-05 |
| 4 | Lysine degradation | 5.8641e-08 | 15 | Hippo signaling pathway | 5.3477e-05 |
| 5 | Fatty acid degradation | 6.6813e-08 | 16 | ECM-receptor interaction | 7.7605e-05 |
| 6 | Prion disease | 1.7778e-07 | 17 | Proteoglycans in cancer | 9.8458e-05 |
| 7 | Fatty acid metabolism | 1.3189e-06 | 18 | Hepatitis B | 0.0005 |
| 8 | Protein processing in ER | 1.4207e-06 | 19 | Prostate cancer | 0.0005 |
| 9 | Thyroid hormone signaling | 2.9598e-06 | 20 | N-glycan biosynthesis | 0.0005 |
| 10 | Cell cycle | 4.6501e-06 | 21 | TGF-beta signaling | 0.0007 |
| 11 | Adherens junction | 7.8950e-06 | 22 | Pathways in cancer | 0.0009 |

FIG. 8E

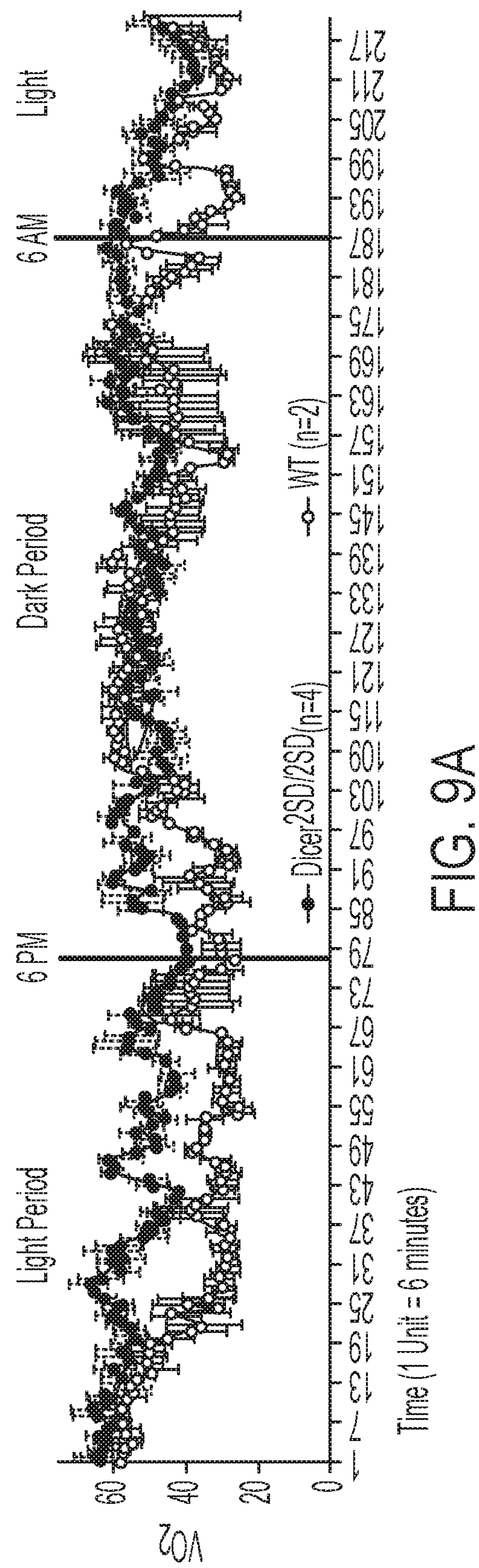
Light Period
6 PM
Dark Period
6 AM
Light
VO2
Time (1 Unit = 6 minutes)
Dicer2SD/2SD(n=4)
WT (n=2)
FIG. 9A
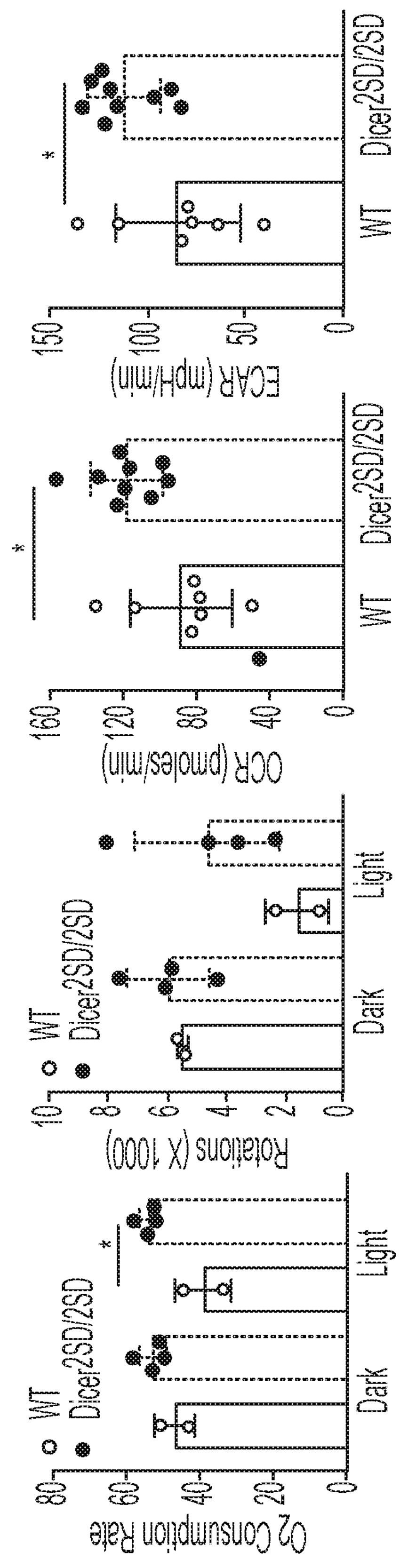
O2 Consumption Rate
WT
Dicer2SD/2SD
Dark
Light
FIG. 9B
Rotations (X 1000)
FIG. 9C
OCR (pmoles/min)
FIG. 9D
ECAR (mpH/min)
FIG. 9E

PHOSPHORYLATED DICER ANTIBODY AND METHODS OF USE THEREOF

The present application is a national phase application under 35 U.S.C. § 371 of International Application No. PCT/US2019/068373, filed Dec. 23, 2019, which claims the priority benefit of U.S. Provisional Applications Ser. No. 62/784,032, filed on Dec. 21, 2018, and 62/812,743, filed on Mar. 1, 2019, the entire contents of each of which being hereby incorporated by reference.

INCORPORATION OF SEQUENCE LISTING

The sequence listing that is contained in the file named "UTFCP1431WO_ST25.txt, which is 10 KB (as measured in Microsoft Windows®) and was created on Dec. 13, 2019, is filed herewith by electronic submission and is incorporated by reference herein.

BACKGROUND

1. Field

The present invention relates generally to the fields of immunology and medicine. More particularly, it concerns anti-dicer antibodies and methods of use thereof.

2. Description of Related Art

Dicer1 is an essential ribo-endonuclease that processes pre-microRNAs into functional microRNAs. DICER1 acts as a haploinsufficient tumor suppressor: somatic heterozygous mutations are frequently observed in human cancers and heterozygosity promotes tumorigenesis in several murine tumor models. DICER1 syndrome patients carry germline heterozygous mutations in DICER1 (missense and truncating), and present with increased risk for a variety of cancers including pleuropulmonary blastoma, ovarian sex cord stromal tumors, cystic nephroma, and thyroid cancer.

Dicer1 is phosphorylated by ERK in the KRAS signaling axis in C. elegans. In this context, phosphorylated Dicer1 is nuclear and drives the oocyte to embryo transition, indicating a novel role for Dicer1 during this key reprogramming event in development. Recently, it was discovered that Extracellular signal-Regulated Kinase (ERK)-dependent phosphorylation of C. elegans DCR1 at Ser1705 and Ser1833 is essential for oogenesis, while dephosphorylation is essential for progression of embryogenesis (Drake, et al., 2014). Thus, oscillation of Dicer1 phosphorylation and dephosphorylation is essential for oogenesis and embryogenesis. This discovery highlighted, for the first time, that Dicer1 function is under tight post-translational control during development. In mammals, it was found that Dicer1 is phosphorylated at the conserved Serines in mouse embryonic fibroblasts (MEFs) and human embryonic kidney cell lines upon fibroblast growth factor stimulation. Moreover, Dicer1 is phosphorylated at Ser1712 and Ser1836 in the developing mouse uterine glands in vivo. In all of these cases, phosphorylation of Dicer1 was coupled with its translocation from the cytoplasm to the nucleus.

Burger et al. identified an additional Serine that is phosphorylated by ATM/ATR during DNA damage response resulting in translocation of Dicer1 from cytoplasm to the nucleus in cultured human cells (Burger, et al., 2017). These results suggest that phosphorylation of Dicer1 is a conserved event; however, the role of Dicer1 phosphorylation and dephosphorylation in vivo in mammals remains unknown.

SUMMARY

In a first embodiment, the present disclosure provides an isolated monoclonal antibody, wherein the antibody specifically binds to phosphorylated human Dicer1 (pDicer1) at Serine 1728 and/or Serine 1852. In particular aspects, the antibody specifically binds phosphorylated human Dicer1 (pDicer1) at Serine 1852. In some aspects, the antibody comprises CDRs 1-3 (SEQ ID NOs: 3 (GYSFTSYW), 5 (IYPGNSAT), and 7 (TRVGYRYEAWFAY)) of the $V_H$ domain and CDRs 1-3 (SEQ ID NOs: 11 (SSVSY), 13 (DTS), and 15 (FQGSGYPLT)) of the $V_L$ domain of the antibody encoded by anti-phospho-Ser1852-DICER1 antibody hybridoma clone 25 (hereinafter referred to as "clone 25"). In specific aspects, the antibody does not bind or has essentially no binding to non-phosphorylated Dicer1. In particular aspects, the antibody recognized the peptide sequence VPR[pS]PVREL only when phosphorylated at the serine ([pS]).

In some aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the $V_H$ domain (SEQ ID NO: 2) of clone 25 and a $V_L$ domain at least about 80% (e.g., 85%, 86%, 87%, 88%, 89%, 90%, 91%, 92%, 93%, 94%, 95%, 96%, 97%, 98%, or 99%) identical to the $V_L$ domain (SEQ ID NO: 10) of clone 25. In some aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the amino acid sequence encoded by SEQ ID NO: 1 and a $V_L$ domain at least about 80% (e.g., 85%, 86%, 87%, 88%, 89%, 90%, 91%, 92%, 93%, 94%, 95%, 96%, 97%, 98%, or 99%) identical to the amino acid sequence encoded by SEQ ID NO: 9. In certain aspects, the antibody comprises a $V_H$ domain identical to the $V_H$ domain (SEQ ID NO: 2) of clone 25 and a $V_L$ domain identical to the $V_L$ domain (SEQ ID NO: 10) of clone 25. In certain aspects, the antibody comprises a $V_H$ domain identical to the amino acid sequence encoded by SEQ ID NO: 1 and a $V_L$ domain identical to the amino acid sequence encoded by SEQ ID NO: 9.

In certain aspects, the antibody is recombinant. In some aspects, the antibody is an IgG, IgM, IgA or an antigen binding fragment thereof. In certain aspects, the antibody is a Fab', a F(ab') 2, a F(ab') 3, a monovalent scFv, a bivalent scFv, or a single domain antibody. In some aspects, the antibody is a human, humanized antibody or de-immunized antibody. In additional aspects, antibody is conjugated to an imaging agent, a chemotherapeutic agent, a toxin or a radionuclide.

In another embodiment, there is provided a composition comprising an antibody of the embodiments (e.g., an antibody binding phosphorylated human Dicer1) in a pharmaceutically acceptable carrier. Further provided herein is an isolated polynucleotide molecule comprising a nucleic acid sequence encoding an antibody of the embodiments (e.g., an antibody binding phosphorylated human Dicer1). In additional embodiments, an isolated polynucleotide molecule comprises SEQ ID NOs: 4, 6 and 8 or SEQ ID NOs: 12, 14 and 16. In yet other embodiments, an isolated polynucleotide comprises SEQ ID NOs: 4, 6, 8, 12, 14 and 16. In still other embodiments, an isolated polynucleotide comprises a sequence having 85%, 86%, 87%, 88%, 89%, 90%, 91%, 92%, 93%, 94%, 95%, 96%, 97%, 98%, 99% or 100% identity to SEQ ID NO: 1 or SEQ ID NO: 9. Also provided herein is a recombinant polypeptide comprising an antibody $V_H$ domain comprising CDRs 1-3 of the $V_H$ domain of clone 25 and CDRs 1-3 of the $V_H$ domain of clone 25. In another embodiment, there is provided an isolated polynucleotide molecule comprising a nucleic acid sequence encoding a polypeptide comprising an antibody $V_H$ domain comprising CDRs 1-3 of the $V_H$ domain of clone 25 and CDRs 1-3 of the $V_H$ domain of clone 25. Further provided herein are expression vectors comprising SEQ ID NO: 1 and/or SEQ ID NO: 9. In some embodiments, an expression vector comprises SEQ ID NOs: 4, 6 and 8 and/or SEQ ID NOs: 12, 14 and 16.

A further embodiment provides a host cell comprising one or more polynucleotide molecule(s) encoding an antibody of the embodiments (e.g., an antibody binding phosphorylated human Dicer1) or a recombinant polypeptide comprising an antibody $V_H$ domain comprising CDRs 1-3 of the $V_H$ domain of clone 25 and CDRs 1-3 of the $V_H$ domain of clone 25. In some aspects, the host cell is a mammalian cell, a yeast cell, a bacterial cell, a ciliate cell or an insect cell.

Also provided herein is a pharmaceutical composition comprising a pDicer1 antibody of the embodiments and a pharmaceutical carrier. A further embodiment provides a composition comprising an effective amount of a pDicer1 antibody of the embodiments for the treatment of cancer in a subject. Further provide herein is the use of a composition comprising an effective amount of a pDicer1 antibody of the embodiments for the treatment of cancer in a subject. In certain aspects, pDicer1 antibody for use in a method of treating a cancer further comprises a cell penetrating peptide (CPP) and/or a nuclear localization signal (NLS). In certain aspects, a pDicer1 antibody of the embodiments, such as an ScFv, comprises both a CPP and a NLS sequence. Examples for CPPs for use according to the embodiments include, without limitation, peptide segments derived from HIV Tat, herpes virus VP22, the Drosophila Antennapedia homeobox gene product and protegrin I.

An additional embodiment provides a method for treating cancer in a subject comprising administering an effective amount of a pDicer1 antibody of the embodiments to the subject.

In some aspects, the cancer is endometrial cancer, lung cancer, pancreatic cancer, ovarian cancer, pleuropulmonary blastoma, an ovarian sex cord stromal tumor, cystic nephroma, or thyroid cancer (e.g., a thyroid carcinoma). In particular aspects, the cancer is endometrial cancer. In some aspects, the cancer has mutant KRas and/or p53.

In certain aspects, the antibody is administered intravenously, intradermally, intratumorally, intramuscularly, intraperitoneally, subcutaneously, or locally. In particular aspects, the antibody is administered intravenously.

In additional aspects, the method further comprises administering at least a second anticancer therapy to the subject. In some aspects, the second anticancer therapy is a surgical therapy, chemotherapy, radiation therapy, cryotherapy, hormonal therapy, immunotherapy or cytokine therapy.

Also provided herein is method for detecting a cancer in a subject comprising testing for the presence of elevated phosphorylated Dicer1 relative to a control in a sample from the subject, wherein the testing comprises contacting the sample with an antibody of the embodiments. In particular aspects, the method if further defined as an in vitro method.

A further embodiment provides an in vitro method of detecting phosphorylated Dicer1 in a sample comprising detecting an elevated level of phosphorylated Dicer1 by measuring binding of a pDicer1 antibody of the embodiments with a sample. In some aspects, the sample is a tissue biopsy, fine needle aspirate, saliva, urine, or plasma. In certain aspects, the elevated level of phosphorylated Dicer1 as compared to a control identifies the samples as an aggressive cancer sample. In some aspects, the aggressive cancer is aggressive endometrial cancer. In some aspects, the elevated level of phosphorylated Dicer1 as compared to a control indicates a poor prognosis. In specific aspects, the elevated level of phosphorylated Dicer1 is further defined as detecting more than 50% of cells in a sample as positive for phosphorylated Dicer1. In additional aspects, the method further comprises administering a pDicer antibody to a subject identified to have the elevated level of phosphorylated Dicer1.

A further embodiment provides a mouse whose genome comprises a phospho-mimetic Dicer1. In some aspects, phospho-mimetic Dicer1 has serine 1712 and/or serine 1836 replaced with aspartic acid. In certain aspects, phospho-mimetic Dicer1 has serine 1712 and serine 1836 replaced with aspartic acid. In some aspects, phospho-mimetic Dicer1 has serine 1712 replaced with aspartic acid. In particular aspects, phospho-mimetic Dicer1 has serine 1836 replaced with aspartic acid. In some aspects, the mouse is a $Dicer^{S1712D}$, a $Dicer^{S1836D}$ or a $Dicer^{2SD}$ mouse. In particular aspects, the mouse is a $Dicer^{S183D/S183D}$ mouse. In some aspects, the mouse has accelerated aging. In some aspects, the mouse has a hypermetabolic phenotype and/or altered metabolic miRNAs. The mouse may be a female or male mouse. Further provided herein is a cell isolated from a mouse of the embodiments.

Also provided herein is a polypeptide comprising a sequence at least 90% identical to human Dicer1 wherein the serine corresponding to position 1728 and/or the serine corresponding to position 1852 replaced with aspartic acid. Further provided herein is a polynucleotide molecule comprising a sequence encoding the polypeptide of the embodiments.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-5E: Novel Dicer1 alleles and phenotype of homozygous mutants. (A) Sites of Dicer1 phosphorylation are shown. DUF, domain of unknown function; PAZ, Piwi Argonaute and Zwille binding domain; dRBD, double stranded RNA binding domain. (B) Homozygous viability of all Dicer1 mutants was tested by inbreeding heterozygous mutants (nomenclature and associated mutations are listed). Observed and expected number (in parenthesis) of all genotypes are listed. WT, wild type; Het, heterozygous mutants; Homo, homozygous mutants. Chi square tests were performed and p-values are listed. (C) Representative images of one week-old (top) and two week-old (bottom) $Dicer^{2SD/2SD}$ mice (asterisk) and normal littermates. (D) One to ten month-old wild type (WT), $Dicer^{S1836D/S1836D}$ and $Dicer^{2SD/2SD}$ male (left, n=12, 12, and 10 respectively) and female (right, n=12, 9, and 11 respectively) mice were weighed regularly. Average weights with standard deviations at multiple time points (in months) are presented. At least 3 mice were present for all genotypes at the end-point (some animals died before reaching end point). (E) Fertility of all homozygous mutants was tested by mating with wild type mice. Number of litters and average litter size for all mutants (males and females) are listed.

FIGS. 6A-6F: Accelerated aging phenotypes in $Dicer^{2SD/2SD}$ mice. (A) Representative micro-CT scans (isosurface threshold 1000) of wild type and $Dicer^{2SD/2SD}$ mouse skeletons. (B) Kyphosis index for wild type (n=4) and $Dicer^{2SD/2SD}$ mice (n=4) was quantified, averaged, and is presented with standard deviation. Student's t-test was used to determine significance, *p=0.02. (C) Bone volume fraction (BVF) in the spine of wild type (n=4) and $Dicer^{2SD/2SD}$ mice (n=4) was quantified, averaged, and is presented with standard deviation. Student's t-test was used to determine significance, *p=0.0003. (D) Bone mineral density (BMD) of spine for wild type (n=4) and $Dicer^{2SD/2SD}$ mice (n=4) was quantified, averaged, and is presented with standard deviation. Student's t-test was used to determine significance, p=0.008. (E) Representative H&E longitudinal sections of the femoral diaphysis (1.25×) from six month old wild type and $Dicer^{2SD/2SD}$ mice. Measurements are shown for thinnest section of the cortical bone. (F) Representative H&E sections of testes (20×), ovaries (10×), skin (20×), and femoral epiphyses and metaphyses (5×) from eight month old wild type and $Dicer^{2SD/2SD}$ mice. Leydig cells (arrow) in testes section, ovarian parenchyma (asterisk), subcutaneous adipose (I) in skin, irregular thickness of growth plate cartilage (arrow) and replacement of physeal cartilage by bone (arrow head) and adipocyte infiltration (star) in the femoral epiphyseal bone marrow are marked. (G) Survival curve of wild type (n=57), $Dicer^{S1712D/S1712D}$ (n=15), $Dicer^{S1836D/S1836D}$ (n=21) and $Dicer^{2SD/2SD}$ (n=21) mice followed for 560 days. Vertical lines represent animals euthanized without morbidity.

FIGS. 8A-8E: Phosphorylation alters Dicer1 localization and miRNA profile. (A) Immuno-fluorescence with an anti-Dicer1 antibody on representative testes sections (20×) from wild type (WT), $Dicer^{S1712D/S1712D}$, $Dicer^{S1836D/S1836D}$ and $Dicer^{2SD/2SD}$ mice. Scale bars=10 μm. (B) Percentage of spermatocytes (excluding spermatids and spermatozoa) with nuclear Dicer1 was calculated in the seminiferous tubules of three wild type (WT), $Dicer^{S1712D/S1712D}$, $Dicer^{S1836D/S1836D}$ and $Dicer^{2SD/hu\ 2SD}$ testes. Cells were binned as cytoplasmic or nuclear/both. Average was calculated with standard deviation. (C) Differential expression of miRNAs in testes (n=3 for Dice$^{2SD/2SD}$ and n=2 for WT) and MEFs (n=4 for Dicer$^{2SD/hu\ 2SD}$ and n=3 for WT) from wild type and Dicer$^{2SD/2SD}$ mice. Green, red, and yellow dots represent downregulated, upregulated, and unaffected miRNAs, respectively, in Dicer$^{2SD/2SD}$ samples as compared with wild type samples. Blue lines represent 2-fold cutoff. (D) Number of downregulated miRNAs (>10 reads/million, and >2 fold difference), and overlap in mutant testes and MEFs. Overlapping miRNAs are listed. (E) Pathway analysis of downregulated miRNAs in mutant testes was performed using DIANATOOLS. Top 22 pathways on the list are presented.

FIGS. 9A-9E: Higher metabolism in Dicer$^{2SD/2SD}$ mice and MEFs. (A) CLAMS test was used to measure oxygen consumption rate (OCR) of wild type (n=2) and Dicer$^{2SD/2SD}$ mice (n=4) from 10 am to 9 am. Rate of oxygen consumption (VO2) in mL/kg/min with standard deviation is shown for every measurement. Vertical lines separate the light period (6 am-6 pm) and dark period (6 pm-6 am) during the experimental measurements. On X-axis, 1 unit=6 minutes from the beginning of measurement. (B) OCR rates were averaged and grouped into light period and dark periods. Student's t-test was used, *p=0.02 for the light period. (C) CLAMS test was used to measure wheel activity of wild type (n=2) and Dicer$^{2SD/2SD}$ (n=4) mice. Measurements were combined and grouped into light period and dark period. Each dot represents one mouse. (D) Seahorse mito stress test assay was used to measure OCR of wild type (n=7) and Dicer$^{2SD/2SD}$ (n=9) mouse embryonic fibroblasts (MEFs). Average measurements with standard deviation are plotted. Student's t-test was used, *p=0.02. (E) Seahorse glycolytic stress test assay was used to measure extracellular acidification rates (ECAR) of wild type (n=7) and Dicer$^{2SD/2SD}$ (n=9) MEFs. Average measurements with standard deviation are plotted. Student's t-test was used, *p=0.04.

DESCRIPTION OF ILLUSTRATIVE EMBODIMENTS

Figure 1A:
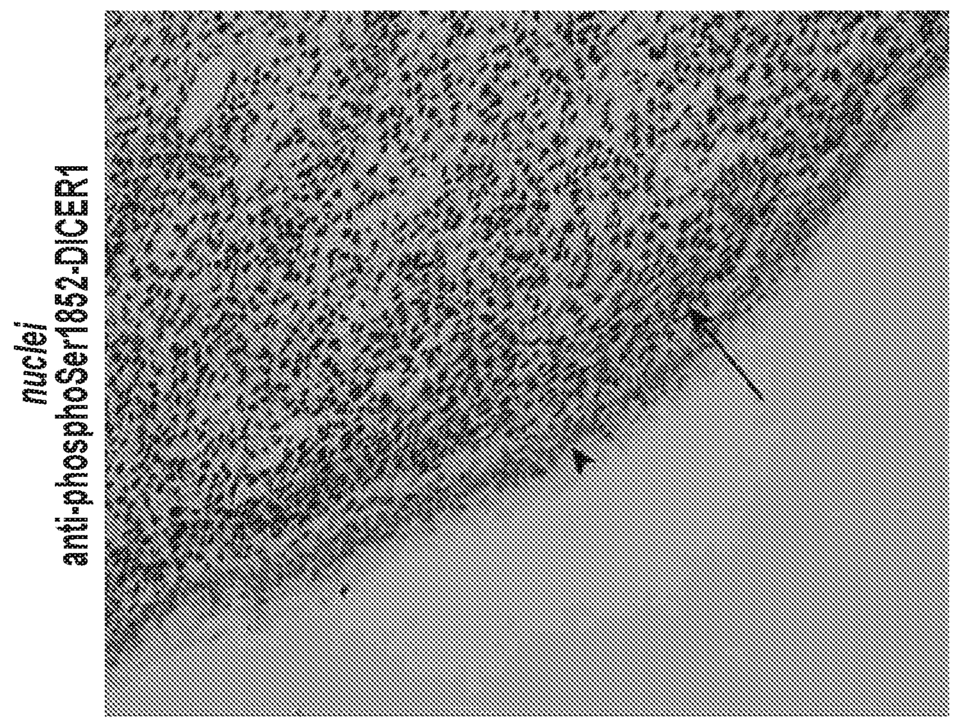
FIGS. 1A-1D: Phosphorylated Dicer is associated with primary endometrial cancers and pleuropulmonary blastoma in humans. (A) Pleuropulmonary blastoma sample displaying positive phosphorylated DICER1 (Serine 1852, Clone 25) staining in the mesenchyme (arrow) predominantly with nuclear localization and absence of staining from the epithelium (blue staining, arrow head). (B) Representative images endometrial cancers stained with anti-phosphorylated DICER1 (Serine 1852, Clone 25) monoclonal Ser1852 antibody, clone 25, named herein as phospho-Dicer for the purposes of figure labeling (top panels) and anti-phosphorylated ERK antibody (bottom panels). (C) Zoom in image of endometrial cancer sample displaying nuclear phosphorylated DICER1 staining. (D) Based on the number of cells that were positive for phospho-Dicer (panel A), the tumors were divided into "low to moderate" positivity for phosphorylated Dicer or "high" positivity for phosphorylated Dicer. Bar graphs display the distribution of tumors with low-to-medium or high phospho-Dicer1 with clinicopathologic feature. BMI, body mass index; LVSI, lymphvascular space invasion; Invasion, depth of myometrial invasion. p=0.002 for BMI, p=0.06 for LVSI, and p=0.03 for depth of myometrial invasion.

DICER1 functions as a tumor suppressor in mouse models. In humans, somatic mutations are associated with many cancers in adults and DICER1 syndrome patients with DICER1 germline mutations are susceptible to childhood cancers. Dicer1 is phosphorylated by the ERK-MAP kinase pathway with essential roles in C. elegans development. Since the ERK-MAP kinase pathway is activated in human cancers, the present studies asked whether phosphorylated Dicer1 contributed to tumor development. In human endometrial cancers, it was discovered that phosphorylated DICER1 is significantly associated with invasive disease. To test a direct involvement of Dicer phosphorylation in tumor development, mice were generated with phospho-memetic alterations at the two conserved Serines phosphorylated by ERK and discovered that constitutive phosphorylation of Dicer1 drives tumor development and dissemination in two independent murine cancer models (KRas+/LA1 and p53+/−). The findings demonstrated that phosphorylated Dicer1 promotes tumor development and invasion.

The phosphorylation sites (Serines 1712 and 1836 in mice, and Serines 1728 and 1852 in humans) and the nuclear localization of phospho-Dicer1 are well conserved in murine and human cells. In the present studies, using phospho-specific antibodies to cognate residues in human DICER1, it was found that DICER1 was phosphorylated in response to fibroblast growth factor activity in cultured human cells. Thus, the role of Dicer1 phosphorylation in tumor development was studied by assaying human primary endometroid endometrial tumors and by generating a phospho-mimetic Dicer1 knock-in mouse model wherein Serines 1712 and 1836 were replaced with Aspartic acids. It was discovered that 1) phosphorylated DICER1 is present in majority of endometrial cancers, and is significantly associated with invasive disease, and 2) constitutive phosphorylation of Dicer1 drives tumor development and dissemination in two independent murine cancer models (KRas$^{+/LA1}$ and p53$^{+/-}$). The present findings demonstrated that phosphorylated Dicer1 is correlated with aggressive human endometrial cancers; and promotes tumor development and invasion in mice in the contexts of oncogenic KRAS and heterozygous p53 backgrounds.

Accordingly, in certain embodiments, the present disclosure provides monoclonal antibodies for phosphorylated DICER1, specifically phosphorylation of serine 1852 of human DICER1. Serine 1852 phosphorylation is necessary and sufficient for nuclear translocation of DICER1. As phosphorylated Dicer1 promotes tumor development and invasion, the present phosphorylated Dicer1 antibody can be used both as a prognostic marker for invasive tumors, and to block the phosphorylated Dicer molecule from its function and arrest tumor progression. Thus, methods are provided herein for the use of the present antibody as a diagnostic, such as to stratify patients with aggressive tumors, and/or for treating cancer, such as lung, pancreatic, ovarian, thyroid or endometrial cancer.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

II. PHOSPHORYLATED DICER ANTIBODIES

In certain embodiments, an antibody or a fragment thereof that binds to at least a portion of phosphorylated Dicer1 and inhibits Dicer signaling are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the pDicer1 antibody is a monoclonal antibody or a humanized antibody, such as the anti-phospho-Ser1852-DICER1 antibody hybridoma clone 25 described below.

```
Clone 25 VH nucleotide sequence
                                          (SEQ ID NO: 1)
CAGGTCCAGCTGCAGCAGTCTGGGACTGTGCTGGCAAGGCCTGGGGCTT
CCGTGAGGATGTCCTGTAAGGCTTCTGGCTACAGCTTTACCAGCTACTG
GATGCACTGGATAAAACAGAGGCCTGGACAGGGTCTAGAATGGATTGGT
GCTATTTATCCTGGAAATAGTGCTACCAACTACAACCAGAAGTTCAAGG
GCAAGGCCAAACTGACTGCAGTCACATCCGCCAGCACTGCCTACATGGA
GCTCAGCAGCCTGACAAATGAGGACTCTGCGGTCTATTACTGTACAAGA
GTGGGCTATAGGTACGAAGCCTGGTTTGCTTACTGGGGCCAAGGGACTC
TGGTCACTGTCTCTGCA

Clone 25 VH amino acid sequence
                                          (SEQ ID NO: 2)
VQLQQSGTVLARPGASVRMSCKASGYSFTSYWMHWIKQRPGQGLEWIGA
IYPGNSATNYNQKFKGKAKLTAVTSASTAYMELSSLTNEDSAVYYCTRV
GYRYEAWFAYWGQGTLVTVSA

Clone 25 VH CDR1 amino acid sequence
                                          (SEQ ID NO: 3)
GYSFTSYW

Clone 25 VH CDR1 nucleotide sequence
                                          (SEQ ID NO: 4)
GGCTACAGCTTTACCAGCTACTGG

Clone 25 VH CDR2 amino acid sequence
                                          (SEQ ID NO: 5)
IYPGNSAT

Clone 25 VH CDR2 nucleotide sequence
                                          (SEQ ID NO: 6)
TATTTATCCTGGAAATAGTGCTAC

Clone 25 VH CDR3 amino acid sequence
                                          (SEQ ID NO: 7)
TRVGYRYEAWFAY

Clone 25 VH CDR3 nucleotide sequence
                                          (SEQ ID NO: 8)
ACAAGAGTGGGCTATAGGTACGAAGCCTGGTTTGCTTAC

Clone 25 VL nucleotide sequence
                                          (SEQ ID NO: 9)
GACATTGTGCTGACCCAGTCTCCAGCAATCATGTCTGCATCTCCAGGGG
AAAAGGTCACCATGACCTGCAGTGCCAGCTCAAGTGTAAGTTACATTCA
CTGGTACCAGCAGAAGTCAAACACCTCCCCCAAACTCTGGATTTATGAC
ACATCCAAACTGGCTTCTGGAGTCCCAGGTCGCTTCAGTGGCAGTGGGT
CTGGAAACTCTTACTCTCTCACGATCAGCAGCATGGAGGCTGAAGATGT
TGCCACTTATTACTGTTTTCAGGGGAGTGGGTACCCGCTCACGTTCGGT
GCTGGGACCAAGCTGGAGCTGAAA

Clone 25 VL CDR1 amino acid sequence
                                         (SEQ ID NO: 10)
DIVLTQSPAIMSASPGEKVTMTCSASSSVSYIHWYQQKSNTSPKLWIYD
TSKLASGVPGRFSGSGSGNSYSLTISSMEAEDVATYYCFQGSGYPLTFG
AGTKLELK

Clone 25 VL CDR1 amino acid sequence
                                         (SEQ ID NO: 11)
SSVSY

Clone 25 VL CDR1 nucleotide sequence
                                         (SEQ ID NO: 12)
TCAAGTGTAAGTTAC

Clone 25 VL CDR2 amino acid sequence
                                         (SEQ ID NO: 13)
DTS

Clone 25 VL CDR2 nucleotide sequence
                                         (SEQ ID NO: 14)
GACACATCC

Clone 25 VL CDR3 amino acid sequence
                                         (SEQ ID NO: 15)
FQGSGYPLT

Clone 25 VL CDR3 nucleotide sequence
                                         (SEQ ID NO: 16)
TTTCAGGGGAGTGGGTACCCGCTCACG
```

Thus, by known means and as described herein, monoclonal antibodies, antibody fragments, and binding domains and CDRs (including engineered forms of any of the foregoing) may be created that are specific to phosphorylated Dicer, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab') 2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made.

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a phosphorylated Dicer1 peptide, in order to produce antibodies specific for phosphorylated Dicer1. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a Dicer antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells ($CD45^+CD5^-CD19^+$) may be isolated from freshly prepared rabbit peripheral blood mononuclear cells of immunized rabbits and further selected for phosphorylated Dicer binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. Phosphorylated Serine 1852 Dicer specific binding Fab may be selected out through multiple rounds enrichment panning and sequenced. Selected Dicer binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165, 464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference.

It is fully expected that antibodies to phosphorylated Dicer Serine 1852 will have the ability to neutralize or counteract the effects of Dicer phosphorylation regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds phosphorylated Dicer1.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against Dicer, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic agent a chelating such diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. METHODS OF TREATMENT

Certain aspects of the present embodiments can be used to prevent or treat a disease or disorder associated with Dicer signaling. Signaling of Dicer may be reduced by any suitable drugs to prevent cancer cell proliferation. Preferably, such substances would be phosphorylated Dicer1 antibodies.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma. In particular embodiments, the cancer is breast cancer.

The cancer may specifically be of the following histological type, though it is not limited to these: neoplasm, malignant; carcinoma; carcinoma, undifferentiated; giant and spindle cell carcinoma; small cell carcinoma; pleuropulmonary blastoma, papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; cosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

A. Pharmaceutical Compositions

Also provided herein are pharmaceutical compositions and formulations comprising a phosphorylated-Dicer1 antibody and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In one aspect, a sHASEGP is combined with one or more additional glycosaminoglycanases such as chondroitinases.

B. Combination Therapies

In certain embodiments, the compositions and methods of the present embodiments involve a pDicer1 antibody in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A pDicer1 antibody may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a pDicer1 antibody is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as y-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs and may be used in combination therapies. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. Exemplary ADC drugs include ADCETRIS® (brentuximab vedotin) and KADCYLA® (trastuzumab emtansine or T-DM1).

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, erb b2 and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., Mycobacterium bovis, Plasmodium falciparum, dinitrochlorobenzene, and aromatic compounds); cytokine therapy, e.g., IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody that may be used. Pembrolizumab, also known as MK-3475, Merck 3475, lambrolizumab, KEYTRUDA®, and SCH-900475, is an exemplary anti-PD-1 antibody. CT-011, also known as hBAT or hBAT-1, is also an anti-PD-1 antibody. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or $V_H$ and/or $V_L$ domains derived therefrom) suitable for use in the present methods can be generated using methods well known in the art. Alternatively, art recognized anti-CTLA-4 antibodies can be used. An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the $V_H$ region of ipilimumab, and the CDR1, CDR2 and CDR3 domains of the $V_L$ region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin.

IV. ARTICLES OF MANUFACTURE OR KITS

An article of manufacture or a kit is provided comprising a pDicer1 antibody is also provided herein. The article of manufacture or kit can further comprise a package insert comprising instructions for using the antibody to treat or delay progression of cancer in an individual. Any of the antibodies or combination therapies described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1-Role of Dicer1 Phosphorylation

Dicer1 phosphorylation at Serines 1705 or 1712 and Serine 1833 or 1836 and nuclear translocation is mediated by Erk downstream of KRas signaling pathway in worms and mice (Drake et al., 2014). Specifically, phosphorylation at Serine 1836 in mice is sufficient to result in nuclear translocation and accelerate aging in mice. To determine whether DICER1 phosphorylation in human tumors at Serine 1852 (which corresponds to Serine 1836 in mice) is correlated with tumor progression, DICER1 phosphorylation status was examined in 54 endometrioid endometrial cancers with increased KRAS or hormonal signaling by immunohistochemistry using anti-phospho-Ser1852-DICER1 (clone 25) and phospho-ERK in a tissue microarray. As no endometrial tumor was obtained with loss of DICER1, two pleuropulmonary blastoma (PPB) tumors from DICER1 syndrome patients were first tested to further test the specificity of anti-phospho-Ser1852-DICER1, clone 25 antibody in human tumors. DICER1 had been found to be absent in the lung epithelium, but positive in the mesenchyme, associated with PPB in 6 of 7 cases (including the two tumors tested here) investigated from patients who carried germline DICER1 mutations (Hill et al., 2009). Phospho-Ser1852-DICER1 (clone 25) antibody that recognizes phosphorylated Serine 1852, positively stained the mesenchyme of the PPB lung tumors, and was negative in the epithelium (FIG. 1A), demonstrating that phosphor-Ser1852-DICER1 clone 25 was specific to DICER1 protein in human tumors. In addition, phosphorylation at Serine 1852 rendered DICER1 to be nuclear as shown previously.

Figure 1B:
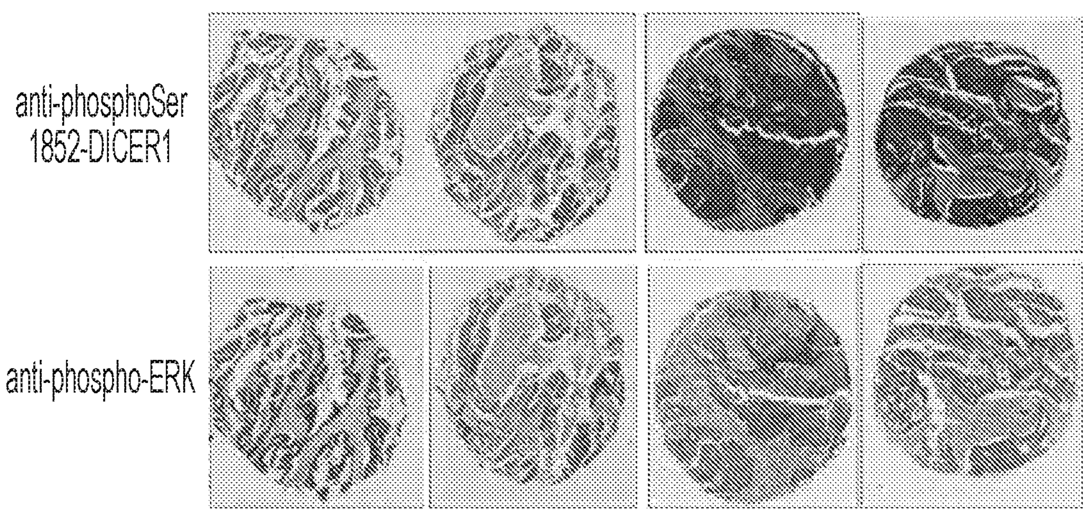
Figure 1C:
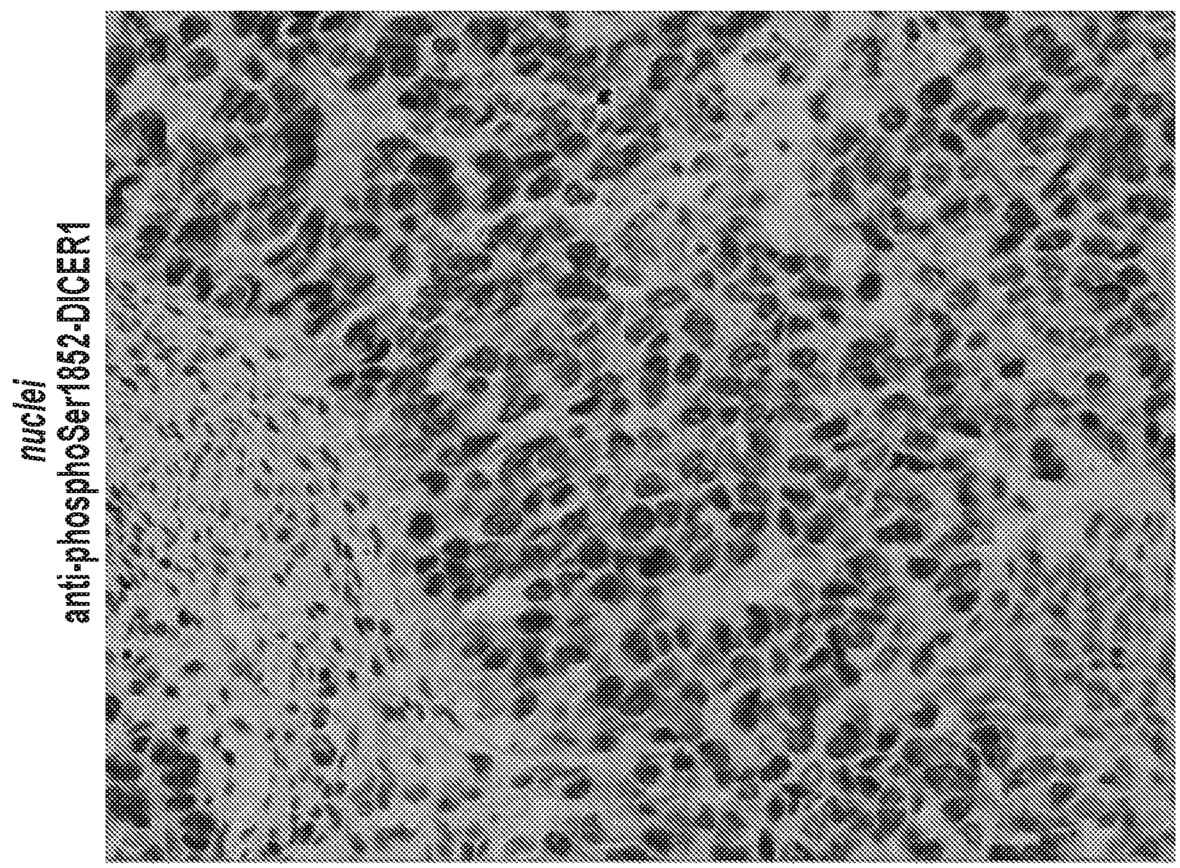
Figure 1D:
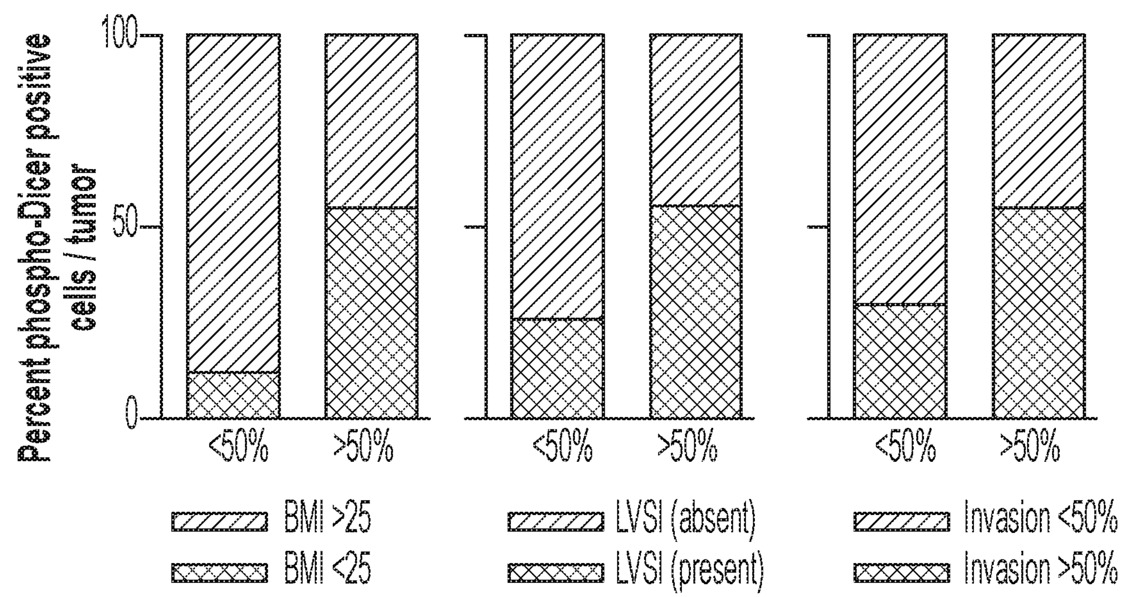

This antibody was then used to assay the 54 endometrioid tumors, that presented with intact DNA mismatch repair (MMR) based on prior microsatellite instability analyses (Billingsley et al., 2015), thus no major MMR-dependent genetic or epigenetic changes were expected in these tumors to influence the molecular analysis. In addition, endometroid tumors with intact MMR pathway do not present with DICER1 mutations, which are often associated with POLE mutations (Billingsley et al., 2015). To examine the status of phospho-DICER1 in these tumors, phospho-Ser1852-DICER1 (clone 25) that recognizes phosphorylated Serine 1852 was used (FIGS. 1B-C). Each tumor with >10% of cells with phospho-Dicer or phospho-ERK signal was called a positive (FIG. 1B). It was observed that 63% (32/51) of endometrioid tumors (three cases were not evaluated due to >2 lost cores of 5 examined for each tumor) were positive for phospho-Dicer1 (FIG. 1B). Overall, 84% of tumors that were positive for phospho-Dicer were also positive for phospho-ERK (27/32) and 5 were negative for phospho-ERK (either nuclear or cytoplasmic). The distribution of phospho-Dicer positive cells did not perfectly overlap with phospho-ERK, which could be an indication of the kinetics of phospho-ERK turnover vs phospho-Dicer turnover due to the presence of different phosphatases. Five tumors that were positive for phospho-Dicer1 did not have a positive signal (>10% of cells) for phospho-ERK. This may indicate that either Dicer1 may be phosphorylated by additional MAPK's or that the perdurance of phospho-Dicer1 is longer than phospho-ERK. To dissect the relationship between phospho-DICER1 levels and clinicopathologic features in endometrioid endometrial cancer, each tumor with less than 50% of cells with phospho-Dicer1 was classified as "low-to-moderate" for Dicer1 phosphorylation (n=35), and tumors with over 50% of cells with phospho-Dicer1 as "high" for Dicer1 (n=16). High phospho-Dicer1 was associated with lower body mass index (p=0.002) and deep myometrial invasion (p=0.03) (FIG. 1D, Table 1). In addition, there was also a trend wherein presence of lymphvascular space invasion (p=0.06) was higher in tumors with high phospho-Dicer1. Deep myometrial invasion and increased lympvascular space invasion is a feature of poor outcome in these cancers. Together, these data indicate that presence of nuclear phosphorylated Dicer1 correlates with endometrial tumor invasion.

TABLE 1

Association between tumor phospho-DICER1 status and demographic and clinicopathologic variables.

| Clinicopathologic Factor | Nuclear phospho-DICER1 Positivity # Low-to Medium (<50%) | # High (>50%) | p value* |
|---|---|---|---|
| Age | | | |
| <60 years | 15 | 7 | 1 |
| ≥60 years | 20 | 9 | |
| BMI | | | |
| <25 (normal or underweight) | 4 | 8 | 0.002 |
| ≥25-30 (overweight) | 30 | 6 | |
| Grade | | | |
| 1 | 18 | 9 | 0.71 |
| 2 | 6 | 1 | |
| 3 | 11 | 6 | |
| Stage | | | |
| I or II | 23 | 8 | 0.36 |
| III or IV | 12 | 8 | |
| LVSI | | | |
| Present | 9 | 9 | 0.056 |
| Absent | 26 | 7 | |
| Depth of invasion | | | |
| <50% | 23 | 5 | 0.03 |
| ≥50% | 12 | 11 | |

*Fisher's exact test

BMI (body mass index) data missing for 3 cases.

LVSI (lymphvascular space invasion)

To determine whether phosphorylated Dicer1 could drive tumor progression in vivo, a Dicer1 knock-in mouse model was generated by replacing Ser1712 and Ser1836 (corresponding to human Serines 1728 and 1852) with aspartic acid, which mimics phosphorylation and renders the protein impervious to dephosphorylation by phosphatases and thus is a model for "constitutive phosphorylation". Dicer1 Serines 1712 and 1836 were replaced with Aspartic acids (Dicer2SD) at the endogenous locus. Both serines were replaced in the mouse model to mimic long term constitutive phosphorylation observed in human tumors. Homozygosity of Dicer1 phospho-mimetic mutations results in high penetrance post-natal lethality (78%), and the few survivors are infertile, display accelerated aging phenotypes. However, the heterozygous mutants were phenotypically normal.

In light of the observations that phospho-DICER1 was present in tumors, it was examined whether phospho-Dicer1 could modulate tumor progression in two independent cancer models. To assess cancer phenotypes independently of developmental lethality displayed by the homozygous mutants, heterozygous Dicer2SD mice were used in two distinct cancer models carrying KRas+/LA1 and p53+/− mutations.

Figure 2A:
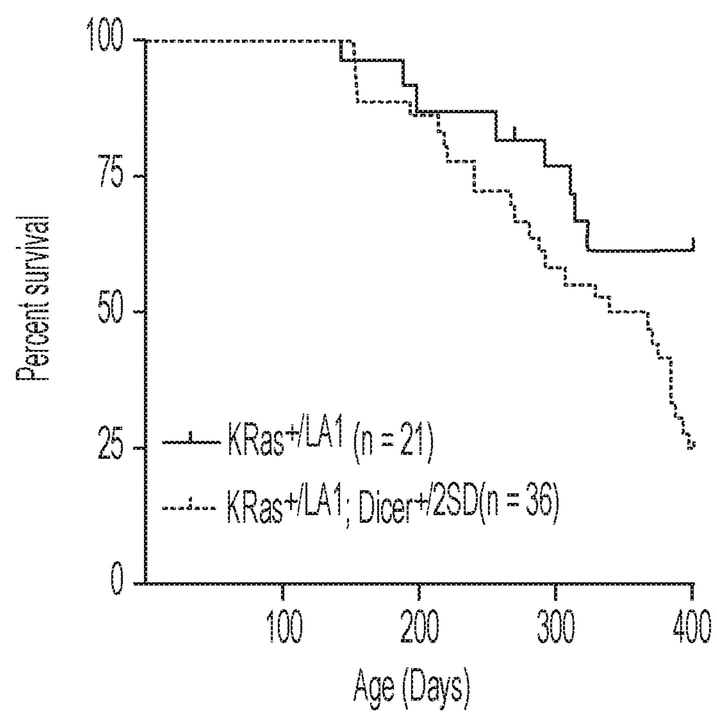
FIGS. 2A-2D: Phospho-Dicer promotes tumorigenesis in $KRas^{+/LA1}$ mice. (A) Kaplan-Meier survival curves of $KRas^{+/LA1}$ mice (n=21) and $KRas^{+/LA1}$; $Dicer^{+/2SD}$ mice (n=36) followed for 400 days. p=0.03. (B) Left: Frequencies of mice with cancer, mutiple cancer, and disseminated cancer incidence in $KRas^{+/LA1}$ mice (n=17) and $KRas^{+/LA1}$. $Dicer^{+/2SD}$ mice (n=24). Right: Tumor types and their frequency, number of mice with >1 tumor types, and the total number of mice with tumors in each genotype. *, metastatic/disseminated tumors. (C) Tumor spectrum of $KRas^{+/LA1}$ mice (n=16 cancers in 17 mice) and $KRas^{+/LA1}$; $Dicer^{+/2SD}$ mice (n=37 cancers in 24 mice). (D) Representative immunofluorescence images captured at 63× displaying phosphorylated Dicer, and DAPI. Heterozygous $KRas^{+/LA1}$ and $Dicer^{+/2SD}$ do not display nuclear phosphorylated Dicer signal, whereas $KRas^{+/LA1}$; $Dicer^{+/2SD}$ and $Dicer^{S2D+/2SD}$ display increased phosphorylated nuclear Dicer signal. Scale bar: 50 microns. Phospho-Dicer detection was assessed with a rabbit polyclonal anti-phospho-Dicer antibody.
Figure 2B:
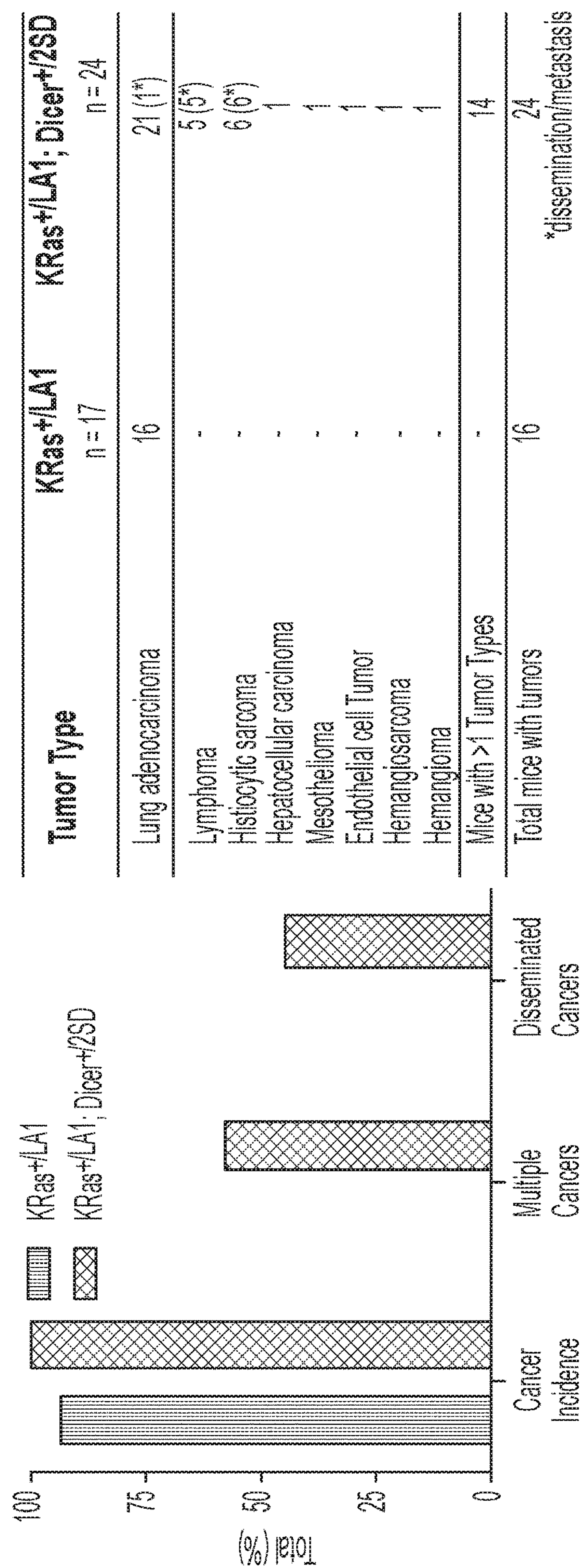
Figure 2C:
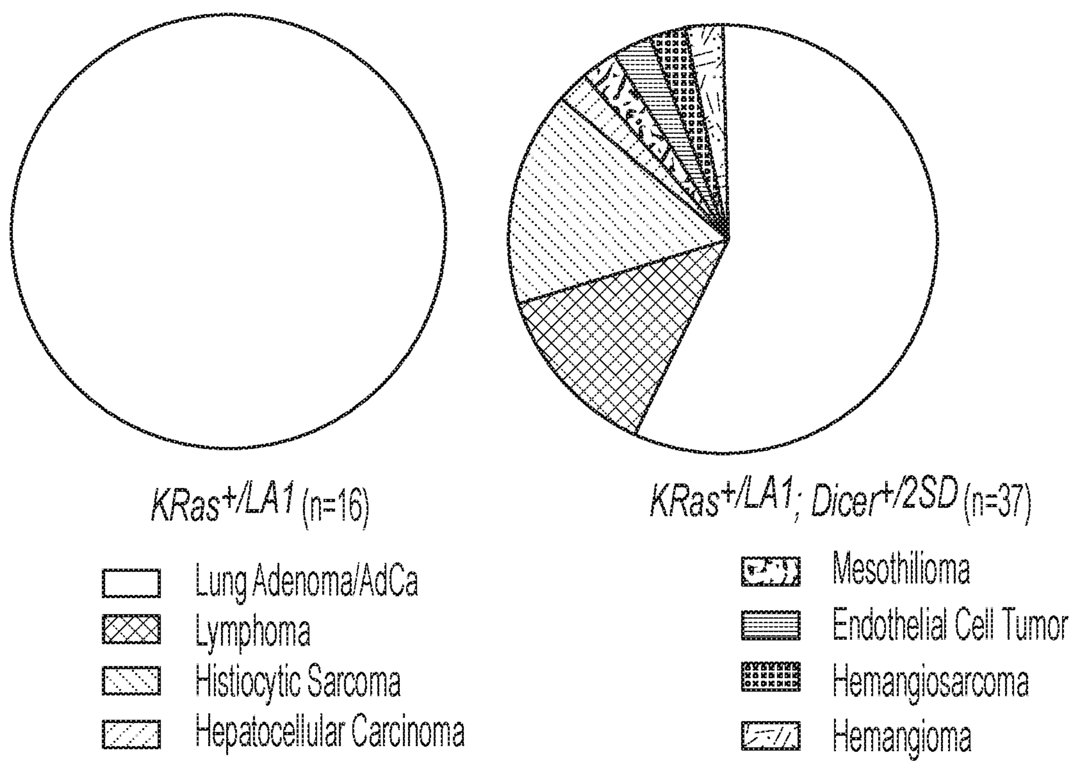
Figure 4A:
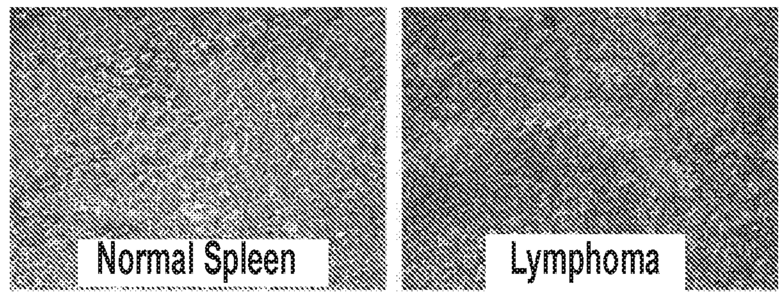
FIG. 4A-4C: Tumors and Metastasis in $KRas^{+/LA1}$; $Dicer^{+/2SD}$ mice. (A) Representative 20×H&E images of normal spleen (left) and splenic lymphoma (right). (B) Representative 20×H&E images of normal liver (left), hepatic lymphoma (middle) and hepatic histiocytic sarcoma (right). (C) Representative 20×H&E images of normal renal cortex (left), renal cortical lymphoma (middle) and pulmonary adenocarcinoma metastasis in renal cortex (right).
Figure 4B:
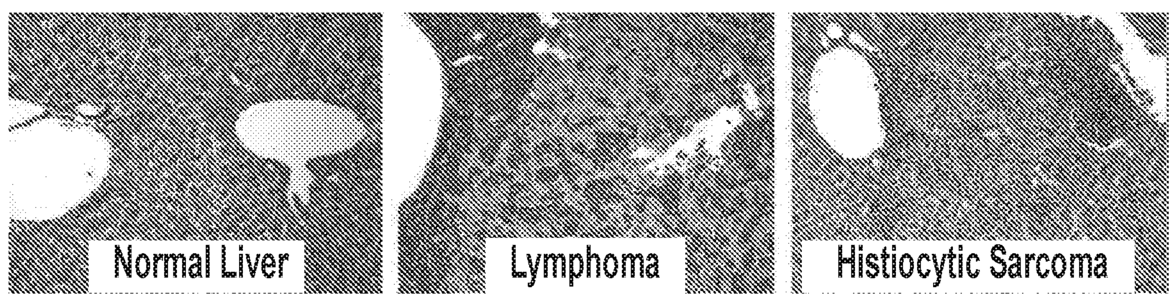
Figure 4C:
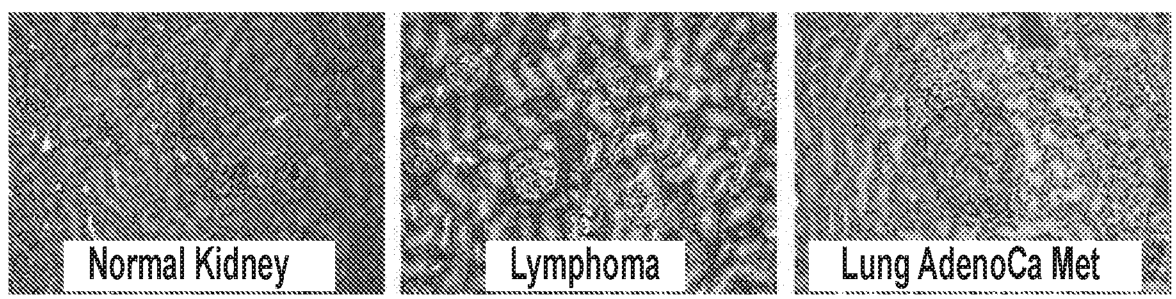

The KRasLA1 allele consists of a duplicated exon1 containing KRasG12D mutation, that undergoes spontaneous recombination of the duplicated exon1 ($10^{-3}$ to $10^{-7}$ cells) yielding either wild type or mutant alleles (Johnson et al., 2001). This model gives rise to fully penetrant multifocal lung cancer starting at one week of age and low frequency thymic lymphomas that vary by the background of the mouse. This tumor model was chosen because heterozygosity of Dicer1 cooperates with KRasG12D lesion to drive lung cancer development in mice; and it was assayed whether heterozygous Dicer2SD would exacerbate KRAS allele, as one phospho-mimetic Dicer1 allele that will generate constitutively phosphorylated Dicer1 protein, and the second can be regulated by KRAS upon phosphorylation (Kumar et al., 2009). In this background, KRas+/LA1; Dicer+/2SD mice developed a wide spectrum of tumors and had a significantly reduced median survival of 353 days as compared with KRas+/LA1 mice which did not achieve median age at the 400-day end point of the study (p=0.03, FIG. 2A). KRas+/LA1 mice developed only lung adenomas/adenocarcinomas (16/17). KRas+/LA1; Dicer+/2SD mice also developed lung adenocarcinomas (21/24); however, 58% of mice (14/24) developed secondary tumors which included 21% lymphomas (5/24, includes 3 animals without lung adenocarcinoma), 25% histiocytic sarcoma (6/24), and one each of hepatocellular carcinoma, mesothelioma, endothelial cell tumor, hemangiosarcoma and hemangioma (FIGS. 2B and 2C). Of note, the lymphomas and histiocytic sarcomas from KRas+/LA1; Dicer+/2SD mice were disseminated into multiple organs of all affected mice including lung, liver, heart, kidney, spleen, and thymus (FIG. 2C). In one KRas+/LA1; Dicer+/2SD mouse, a lung adenocarcinoma metastasized to the kidney and heart (FIG. 4).

Figure 2D:
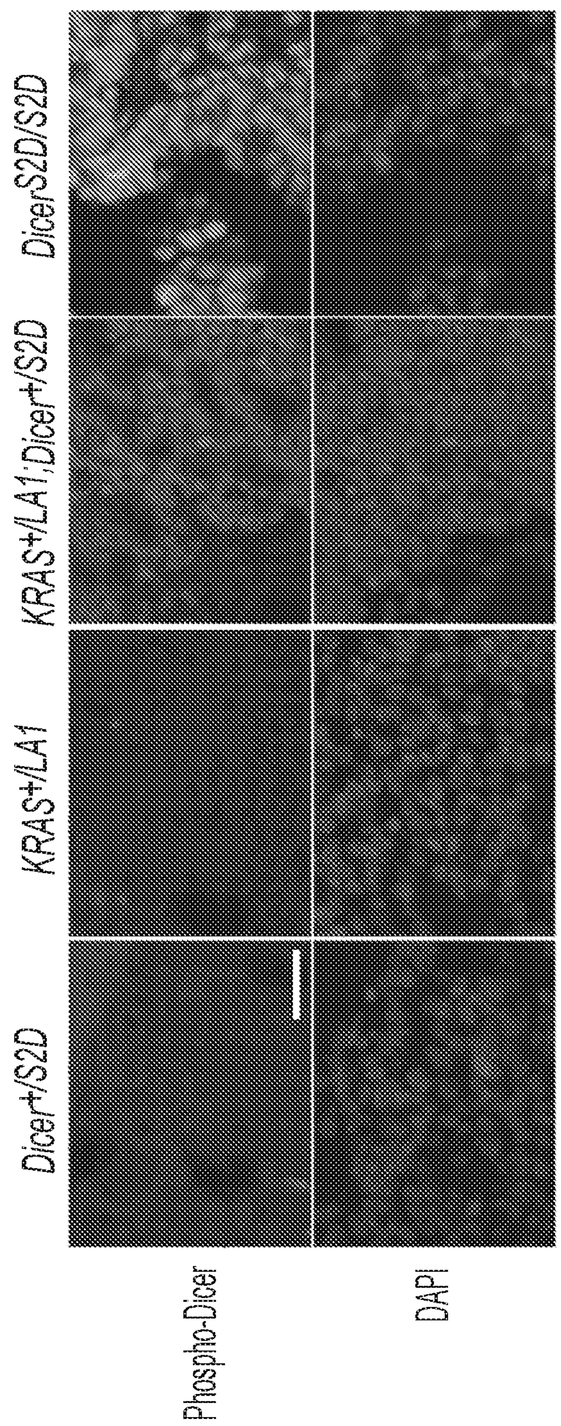

To determine whether the phospho-mimetic Dicer1 protein behaved as a constitutively phosphorylated protein, immunofluorescence was performed on each of the lung tissues from each of genotypes using the phospho-Dicer1. Heterozygous Dicer S2D allele or the KRAS LA1 allele are nearly absent for the phospho-Dicer signal (FIG. 2D). As expected, the homozygous Dicer S2D lung cells displayed 100% positive signal with the antibody, and all the cells with phosphor-Dicer signal displayed nuclear localization. KRas+/LA1; Dicer+/2SD lung sections reveal over 70% of cells with phospho-Dicer (polyclonal antibody to the mouse phosphorylated Dicer1 protein) nuclear and positive signal, indicating that increased KRAS signaling resulted in increased phosphorylation and nuclear translocation of Dicer in this model (FIG. 2E). These results indicated that phospho-mimetic Dicer1 cooperates with oncogenic KRasG12D resulting in a wide spectrum of tumors, and metastases.

Figure 3A:
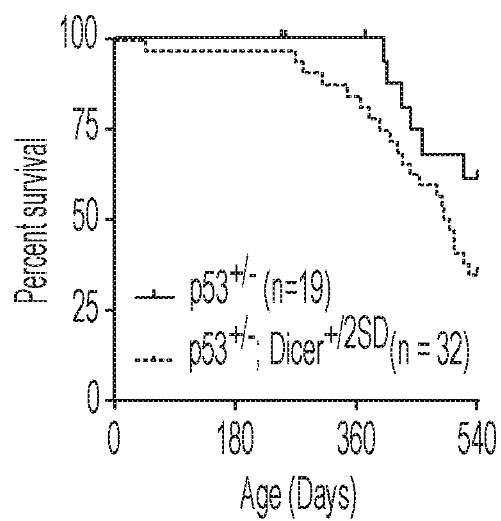
FIGS. 3A-3D: Phospho-Dicer promotes tumorigenesis in $p53^{+/-}$ mice (A) Kaplan-Meier survival curve of $p53^{+/-}$ mice (n=19) and $p53^{+/-}$; $Dicer^{+/2SD}$ mice (n=32) followed for 540 days. p=0.07. (B) Tumor-free survival curve of $p53^{+/-}$ mice (n=12) and $p53^{+/-}$; $Dicer^{+/2SD}$ mice (n=21) followed for 540 days. Kaplan-Meier survival analysis was performed, p=0.03. (C) Left: Frequencies of mice with cancer, multiple cancer, and disseminated cancer incidence in $p53^{+/-}$ mice (n=12) and $p53^{+/-}$; $Dicer^{+/2SD}$ mice (n=21). Right: Tumor types and their frequency, number of mice with >1 tumor type and the total number of mice with tumors in each genotype. *, metastatic/disseminated tumors. (D) Tumor spectrum of $p53^{+/-}$ mice (n=12 mice, 3 cancers in 3 mice) and $p53^{+/-}$; $Dicer^{+/2SD}$ mice (n=21 mice, 20 cancers in 15 mice). Phospho-Dicer detection was assessed with a rabbit polyclonal anti-phospho-Dicer antibody.

TP53 loss is associated with DICER1 mutations and the activated KRAS pathway in many human tumors (Kumar et al., 2009; Pugh et al., 2014; Rakheja et al., 2014). To test whether phosphorylated Dicer1 is sufficient to promote tumorigenesis in the context of p53 heterozygosity, the Dicer2SD allele was next introduced into p53+/− mice which primarily develop osteosarcomas and lymphomas (Jacks, et al., 1994). Similar to the KRas+/LA1; Dicer+/2SD model, p53+/−; Dicer+/2SD mice (n=32) exhibited a reduced median survival of 497 days as compared with p53+/− mice (n=19) which did not achieve median age at the 540-day end point used in this study (p=0.07, FIG. 3A).

Figure 3B:
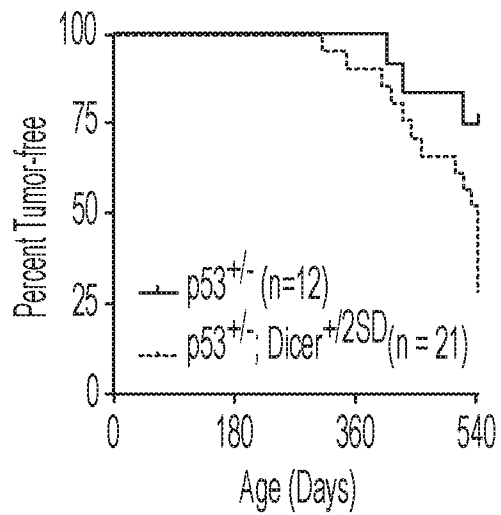
Figure 3C:
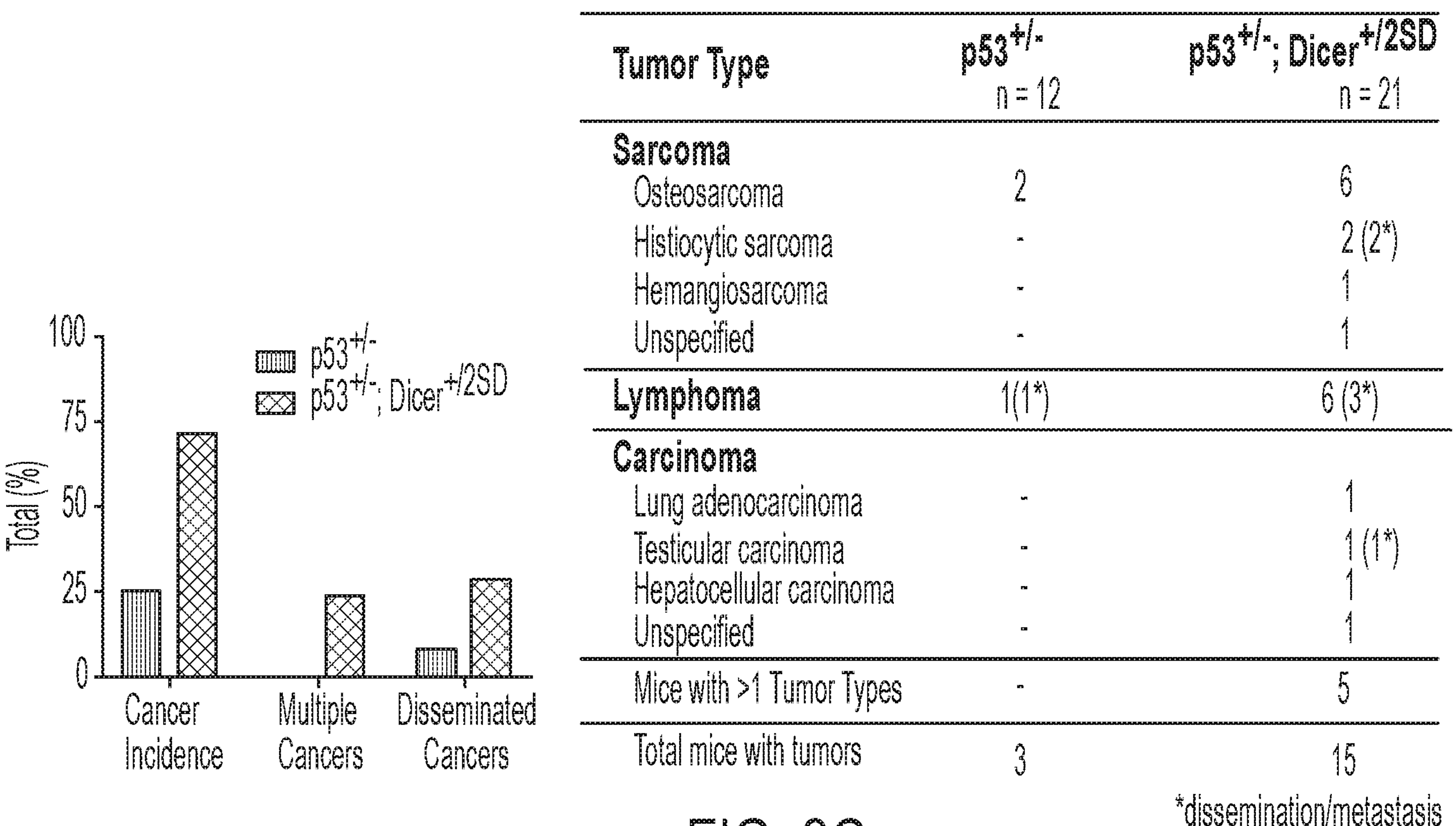
Figure 3D:
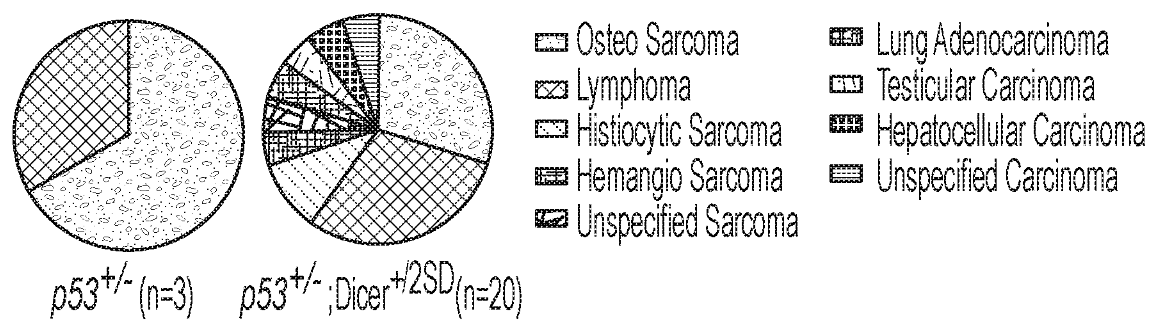

Additionally, p53+/−; Dicer+/2SD mice exhibited a wide spectrum of tumors and had a significantly reduced tumor-free survival as compared with p53+/− mice (p=0.03, FIG. 3B). 71% (15/21) of the p53+/−; Dicer+/2SD mice developed tumors as compared with 25% (3/12) of the p53+/− mice (FIGS. 3B and 3C). In contrast to p53+/− mice which only developed osteosarcomas (n=2) and lymphoma (n=1), the spectrum of tumors in p53+/−; Dicer+/2SD mice included osteosarcomas (n=6), lymphomas (n=6), histiocytic sarcomas (n=2), hemangiosarcoma, lung adenocarcinoma, hepatocellular carcinoma, testicular carcinoma, and two undifferentiated tumors (FIG. 3D). 24% of p53+/−; Dicer+/2SD mice (5/24) displayed multiple cancers including one mouse which developed osteosarcoma, lymphoma and adenocarcinoma (FIGS. 3C-D). Interestingly, lymphomas, histiocytic sarcomas, and a testicular carcinoma were disseminated into many organs as previously observed in KRas+/LA1; Dicer+/2SD mice. None of the p53+/− mice developed multiple cancers.

The role of post-translationally modified Dicer1 in tumorigenesis was unknown. The present studies demonstrated, for the first time, that phosphorylation of Dicer1 cooperates with two distinct oncogenic lesions, KRas+/LA1 and p53+/−, to drive increased tumorigenesis, a diverse tumor spectrum, and metastases. Additionally, the development of multiple cancers in a high percentage of mice indicates that phospho-Dicer1 not only plays a role in tumor development and dissemination, but also sensitizes multiple cell types for tumor development. Finally, these observations in mice coupled with the correlation between phospho-DICER1, using the monoclonal anti-phospho-Serine 1852-DICER1 antibody reveals that DICER1 phosphorylation at Serine 1852 in humans specifically correlates with invasive endometrial cancer indicating that constitutive Dicer1 phosphorylation promotes tumor invasion and metastasis.

Example 2—Materials and Methods

Mouse breeding, maintenance, screening and genotyping: Mice were maintained in >90% C57BL/6 background. All mouse studies were conducted in compliance with an Institutional Animal Care and Use Committee protocol. Live mice were weaned at the age of three weeks, and ear biopsies were collected. The tissues were digested by Lysis buffer (1×PCR buffer, 1% Triton X, 250 μg/μL Proteinase K) at 550° C. overnight, and heated at 950° C. for 15 minutes to denature Proteinase K. 2 μL of the lysed tissue extract was used for PCR reaction to amplify 1 Kb region of the targeted site. The PCR product was gel purified and sanger-sequenced to identify any indels at the target site.

Phosphorylated DICER1 Ser1852 antibody: To detect phosphorylated Dicer in vivo in human tumors a mouse monoclonal antibody was generated to Human DICER1 peptide VPR[pS]PVREL. [pS] is phosphorylated Serine 1852 in human DICER1. The antibody was generated at the MD Anderson Mouse Antibody Facility, through immunization of 3 BALBC mice using the following peptide sequence Cysteine-Valine-Proline-Arginine-phopshoSerine-Proline-Valine-Arginine-Glutamic Acid-Leucine, into the mouse foot pad. Cysteine was added to the C terminal end of the peptide to enable conjugation with KLH for generating the fusions for the monoclonal antibody. After five rounds of injections, the mice were bled and serum tested in an ELISA assay to test response against the peptide. Lymph nodes were drained from the immune responsive mice and fusions of the plasma cells with the murine myeloma counterparts were performed. The fusion (cells) were plated onto 96 well plates and after 9 days, the supernatant from 85 clones were selected and screened against phospho-Dicer Ser1852 peptide, non-phosphorylated DICER1 Ser1852 peptide (this peptide is identical to the phospho peptide Ser1852 except that the Serine is unphosphorylated) and a distinct phospho-peptide, which was used as a control to rule out that the antibody was only detecting the negatively charged phosphorylation site. 59 of the 85 clones produced high to moderate binding specifically to pSer1852-DICER1 peptide and no binding to unphosphorylated Ser1852-DICER1 peptide or a random phospho peptide. 2 clones Clone number 25 and 124 were then tested using immunofluorescence and western analysis for specificity to Dicer Human Embryonic Kidney Cells (HEK). Clone number 25 was very sensitive and specific to phosphorylated human DICER1 and phosphorylation at Serine 25 was sufficient to detect DICER1 in the nucleus (as was shown previously with the polyclonal phosphor-Dicer antibody, generated to C. elegans DCR-1 epitopc). Clone number 25 was then purified by the monoclonal antibody facility at 1 mg/ml concentration and used for Immunohistochemistry and Immuno-fluorescence at 1:200 dilution. Phospho-Ser1852-DICER1 monoclonal antibody clone number 25 was then tested on human tumors from Pleuropulmonary blastoma patients, which are negative for DICER1 in the epithelium but positive in the mesenchyme for specificity in human tumors (FIG. 1A). It was found that anti-phospho-Ser1852-DICER1, clone number 25, positively detected nuclear Dicer1 in the PPB mesenchyme, but not epithelia, as expected, demonstrating that this antibody is specific to DICER1 phosphorylation in human tumors (FIG. 1).

Immunohistochemistry of human endometrial tumors using Tissue MicroArray: Immunohistochemistry was performed on a tumor microarray (TMA) of 54 primary endometrioid endometrial cancer cases. These are untreated tumor samples. Four separate cores were obtained from areas of viable tumor tissue in paraffin blocks of formalin-fixed tumors. The areas for inclusion in the TMA were determined by a gynecologic pathologist (DFC). The tumor microarray was then created as previously described (Fedor and De Marzo, 2005). Practical methods for tissue microarray construction has been previously described (Fedor and De Marzo, 2005). Five micrometer sections of the TMA block were obtained and stained for anti-phospho-Ser1852-DICER1, clone number 25 (2 blocks) (generated as described above, 1:200 dilution), and anti-phospho-ERK (2 blocks). Phospho-ERK staining was performed with anti-phospho-ERK (Thr 202/Tyr 204, #9101 S, rabbit anti-human, Cell Signaling Technology, Inc., Danvers, MA, 1:100 dilution). Slides were then incubated MACH2 Universal polymer-HRP (#M2U522H, BioCare Medical, LLC., Concord CA). Signals were developed with the 3,3'-diaminobenzidine (DAB) substrate DAB+ Liquid (#K3468, Dako Cytomation, Carpintera, CA). Slides were read by two blinded independent examiners (BJR and DFC). Staining for each antibody was reviewed and recorded as a percentage of cells with nuclear stain and a percentage of cells with cytoplasmic stain. The percentages were averaged between examiners.

Mouse Tumor Study: The heterozygous Dicer2SD allele was crossed into the KRas+/LA1 tumor model, which specifically develops lung tumors with 100% penetrance. A cohort containing 21 KRas+/LA1 mice and 36 KRas+/LA1; Dicer+/2SD mice was generated. The cohort was monitored for 400 days. Moribund animals were euthanized, and their tissues were collected. Animals that were still alive at 400 days were sacrificed and their tissues were collected for pathology. Animals that were euthanized due to non-tumor related issues (dermatitis, rectal prolapse) were not included in the study. Tissues from 17 KRas+/LA1 mice and 24 KRas+/LA1; Dicer+/2SD mice were collected for pathological examination. Tissue sections were prepared as the tissues became available, and examined together when all samples were ready.

Similarly, the mutant Dicer allele was introduced into the p53+/– driven tumor model. A cohort containing 19 p53+/– mice and 32 p53+/–; Dicer+/2SD mice was generated. The cohort was monitored for 540 days. Moribund animals were euthanized, and their tissues were collected. Animals that were still alive at 540 days were sacrificed and their tissues were collected for pathology. Animals that were euthanized due to non-tumor related issues (dermatitis, rectal prolapse) were not included in the study. Tissues from 12 p53+/– mice and 21 p53+/–; Dicer+/2SD mice were collected for pathological examination. Tissue sections were prepared as the tissues became available, and examined together when all samples were ready.

Histopathology: Tissues harvested from mice were fixed in 10% neutral buffered formalin and paraffin-embedded. Four micrometer sections were stained with hematoxylin and eosin, and examined by light microscopy. Tissue processing, paraffin embedding, sectioning, and H&E staining were performed by the MD Anderson Department of Veterinary Medicine & Surgery Histology Laboratory.

Statistical Analysis: Student's t-tests, Fisher's exact tests and Kaplan-Meier survival analyses were performed using GraphPad Prism 7 Software. P-values were calculated using Log-rank (Mantel-Cox) test and $p<0.05$ was considered statistically significant.

Immuno-fluorescence staining: Tissues harvested from mice and fixed in 10% neutral buffered formalin and paraffin-embedded. Tissue processing, paraffin embedding, sectioning, as performed by the MD Anderson Department of Veterinary Medicine & Surgery Histology Laboratory. Immuno-fluorescence to detect for phosphorylation status of Dicer was conducted with phospho-Dicer specific antibody (1:200, generated in house), and DAPI (to mark DNA). For each genotype, 50 images at 63× were captured across the full slides. Each image captured 200-500 cells. To avoid bias, the staining and image capture and analysis was performed in a blinded manner.

Example 3—Further Characterization of Phosphorylated Dicer1

Figures 5A, 5B:
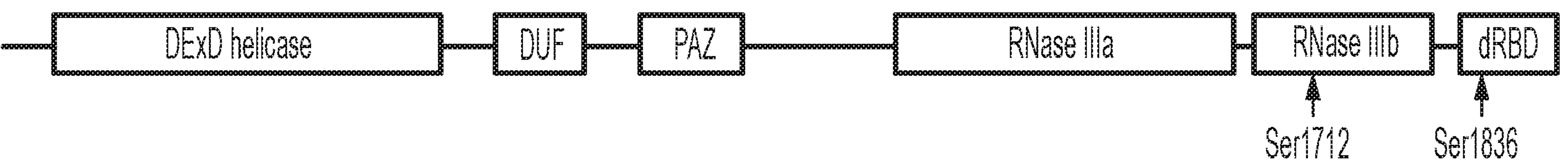

Phosphorylation at Ser1836 in mice impairs Dicer1 function: To examine the role of phosphorylation-mediated regulation of Dicer1 function in mammals, three phospho-mimetic Dicer1 knock-in mouse models were generated (FIGS. 5A, 5B). Mice with Ser1712 replaced with aspartic acid (Dicer$^{S1712D}$) were generated using CRISPR/Cas9 technology. Mice with Ser1836 replaced with aspartic acid (Dicer$^{S1836D}$), and both Ser1712 and Ser1836 replaced with aspartic acids (Dicer$^{2SD}$) were obtained using the traditional ES cell technology. Additionally, CRISPR/Cas9 mediated targeting also resulted in generation of Dicer1 alleles with frame shift truncation starting at position 1712 (Dicer"), and 3 bp in-frame deletion of codon 1712 (Dicer$^{\Delta1712}$).

Dicer1-null mice are embryonic lethal at E7.5 (Bernstein et al., 2003). To determine if phospho-mimetic Dicer1 alleles mimicked loss of Dicer1 activity, lethality was assayed for in homozygous mutant mice for each allele generated. Dicer$^{S1712D/S1712D}$ and Dicer$^{\Delta1712/\Delta1712}$ mice were born at the expected Mendelian ratios (FIG. 5B). Dicer-mice, as expected, were embryo lethal. Dicer$^{S1836D/S1836D}$ mutants were born but only 11% of progeny (11/103) were homozygous mutants at weaning instead of the expected 25% frequency indicating partial lethality (p=0.003, FIG. 1B). Dicer2-SD/SD mice, like the Dicer$^{S1836D/S1836D}$ mice, were also partially lethal as only 7% of progeny (8/115) were homozygous mutants at weaning ($p<0.001$). Examination of E18.5 embryos from Dicer$^{+/2SD}$ heterozygous crosses revealed that homozygous mutant embryos were viable. Of the 42 embryos examined, 10 were wild type, 22 were heterozygous, and 10 were homozygous mutants. Histopathologic examination of E18.5 embryos did not reveal any defects in homozygous mutants; however, dead pups were observed within four days after birth that were genotyped as homozygous mutants suggesting that lethality is postnatal. Combined, these data reveal that constitutive phosphorylation at Ser1836 impairs Dicer1 function, and causes post-natal lethality.

Next, it was examined if mutant Dicer1 alleles are functionally hypomorphic by introducing a null allele over each mutant background. $Dicer^{S1836D/-}$ and $Dicer^{2SD/-}$ mice were non-viable, while the $Dicer^{S1712D}/-$ and $Dicer^{\Delta1712}/-$ mutants were viable. These data demonstrated that constitutive phospho-mimic or deletion of Ser1712 has seemingly no impact on Dicer1 functions, whereas phospho-mimic at Ser1836 is sufficient to alter Dicer1 functions with lethal consequences.

Studies have shown that Dicer1 loss activates the p53 pathway (Mudhasani et al., 2008). It was therefore genetically tested whether post-natal lethality in $Dicer^{2SD/2SD}$ mice is p53 dependent by concomitantly deleting p53 in the Dicer2SD/2SD background. Of the 72 progeny born from $Dicer^{+/2SD}$ $p53^{+/-}$ intercrosses, none were $Dicer^{2SD/2SD}$ $p53^{-/-}$ (p=0.01). This result indicated that loss of p53 does not rescue the post-natal lethality in the $Dicer^{2SD/2SD}$ mice suggesting a distinct pathway is responsible for lethality.

Figures 5C, 5D:
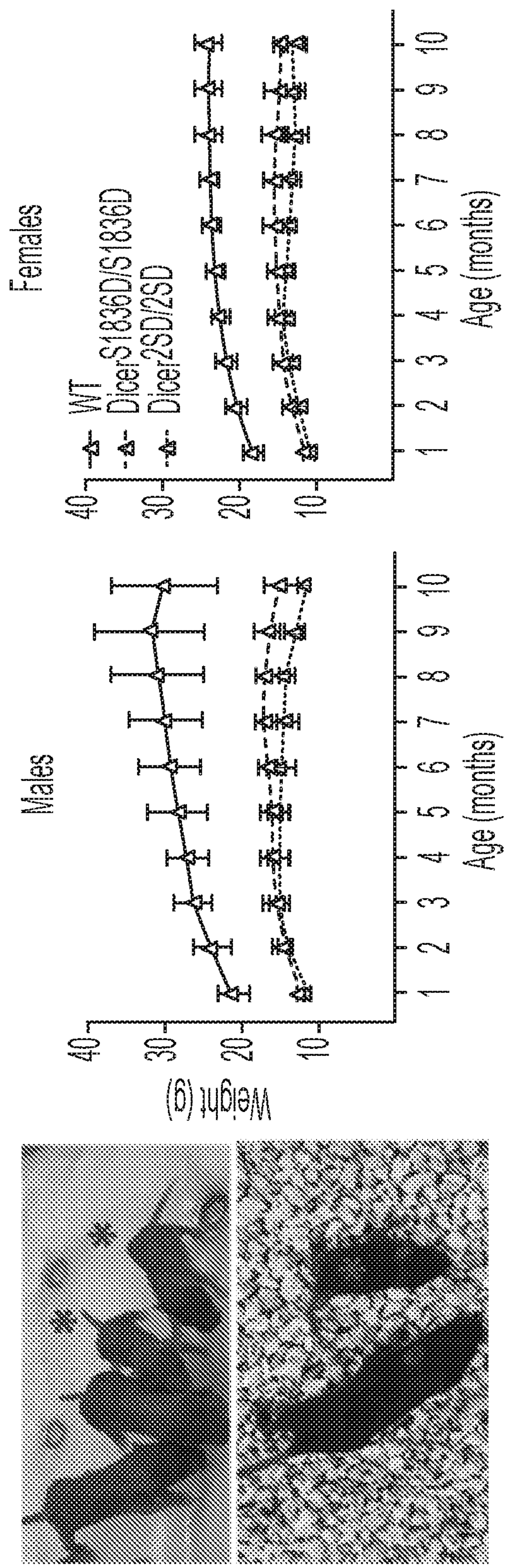

Constitutive Dicer1 phosphorylation at Ser1836 leads to growth retardation and infertility: To determine whether the $Dicer^{S1836D/S1836D}$ and $Dicer^{2SD/hu\ 2SD}$ mice that survived post-natal lethality displayed developmental defects, survivors were extensively characterized and multiple striking defects were found. The most obvious of these defects was growth retardation. Both male and female $Dicer^{S1836D/S1836D}$ and $Dicer^{2SD/2SD}$ survivors displayed a 35-50% reduction in size as compared to their wild type sex-matched littermates, and the growth retardation phenotype persisted throughout their lifespan (FIGS. 5C and 5D). $Dicer^{S1836D/S1836D}$ and $Dicer^{2SD/2SD}$ mice also displayed fertility defects as assayed via housing homozygous mutant males with wild type females and vice versa. $Dicer^{S1712D/S1712D}$ and $Dicer^{\Delta1712/\Delta1712}$ mice were fertile and produced 8-9 progeny per litter (FIG. 5E); however, $Dicer^{S1836D/S1836D}$ and $Dicer^{2SD/2SD}$ mice (both males and females) did not give rise to any progeny (FIG. 5E). These results suggest that constitutive Dicer1 phospho-mimic at Ser1836 is sufficient to drive early post-natal lethality, retard growth, and cause infertility. $Dicer^{2SD/2SD}$ mice display similar phenotypes with greater magnitude (increased post-natal lethality and growth retardation) as compared with $Dicer^{S1836D/S1836D}$ mice. Thus, on $Dicer^{2SD/2SD}$ mice were focused from this point forward.

Figures 6E, 6G:
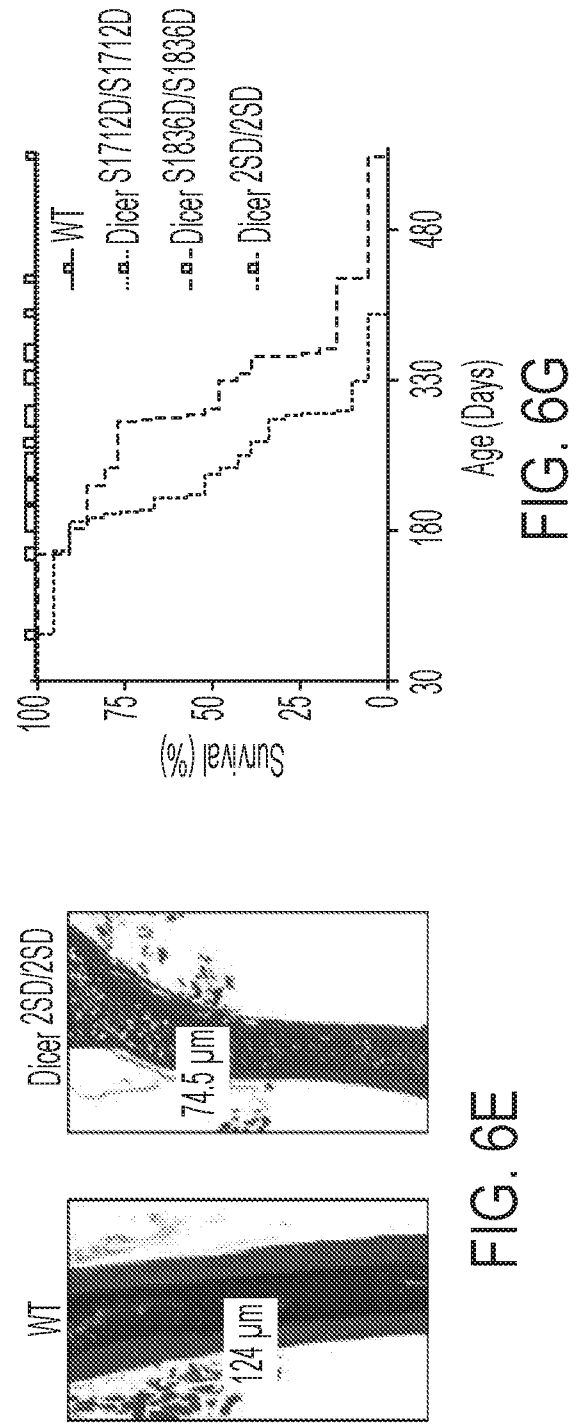
Figure 6F:
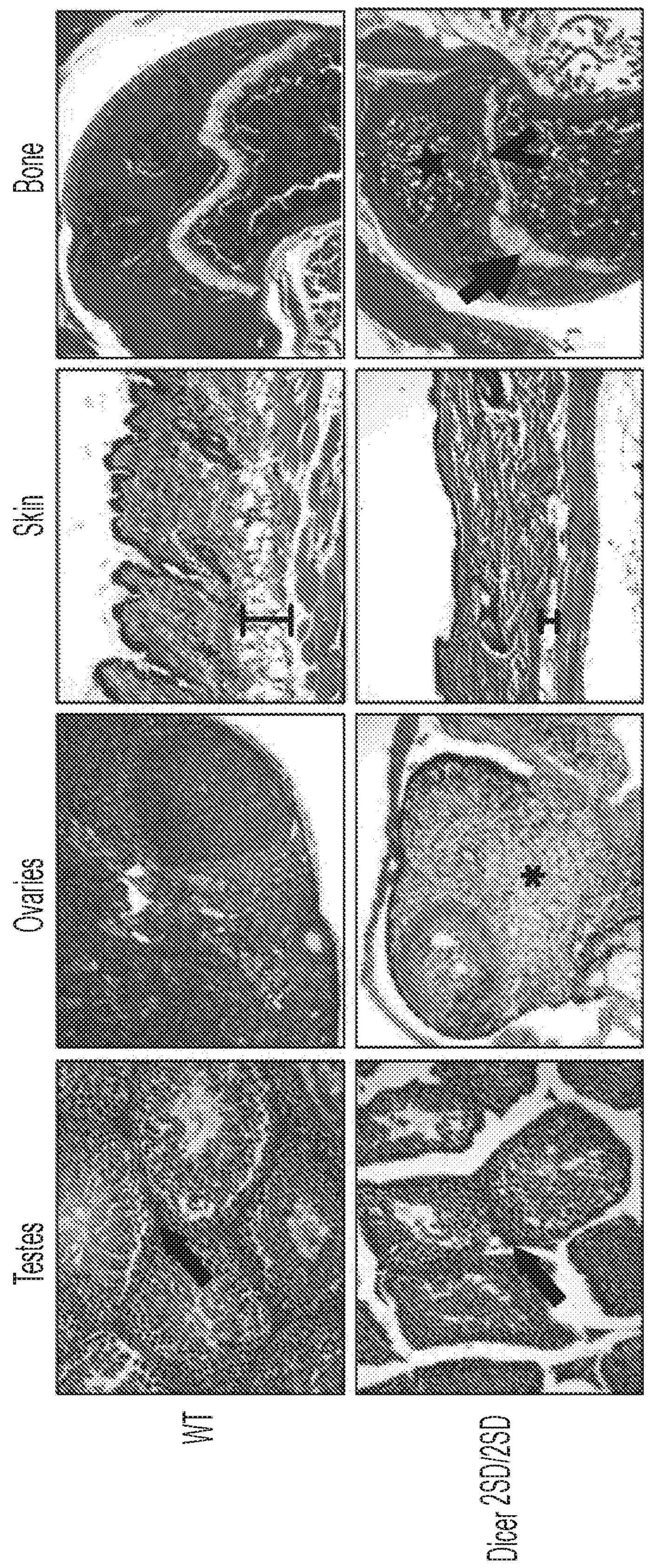
Figure 7A:
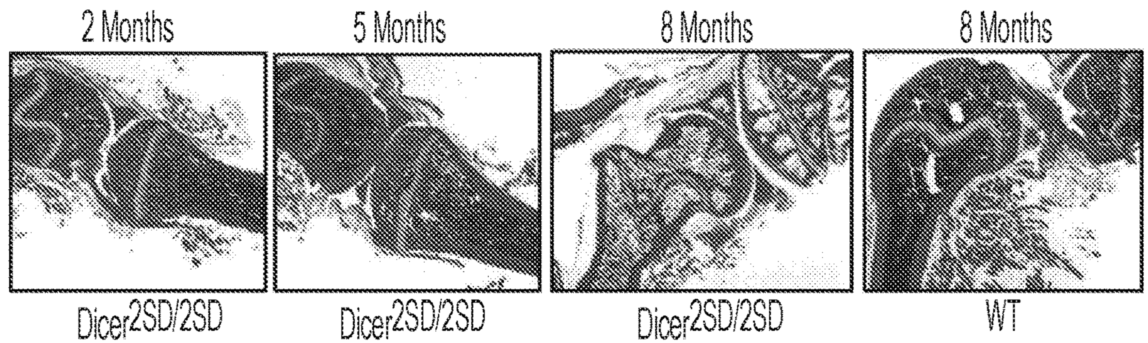
FIGS. 7A-7C: Hematological Phenotypes of $Dicer^{2SD/2SD}$ Mice. (A) Representative H&E sections of the femur and tibia from 2-8 month-old $Dicer^{2SD/2SD}$ mice and an 8 month-old wild type mouse. (B) Complete blood counts of 2-8 month-old wild type (n=7) and $Dicer^{2SD/2SD}$ littermate mice (n=8). Average measurement with standard deviation is shown. p=0.89 for platelets, **p=0.007 for RBC and *p=0.01 for WBC. Each dot represents a mouse. WBC, white blood cell; RBC red blood cell. (C) Serum enzyme levels in the blood of 2-8 month-old wild type (n=7) and $Dicer^{2SD/2SD}$ littermate mice (n=8). Average measurement with standard deviation is shown. p=0.11 for AST, p=0.16 for ALT, and *p=0.01 for AP. Each dot represents a mouse. AST, aspartate aminotransferase; ALT, Alanine transaminase; AP, alkaline phosphatase; U/L, units per liter.
Figure 7B:
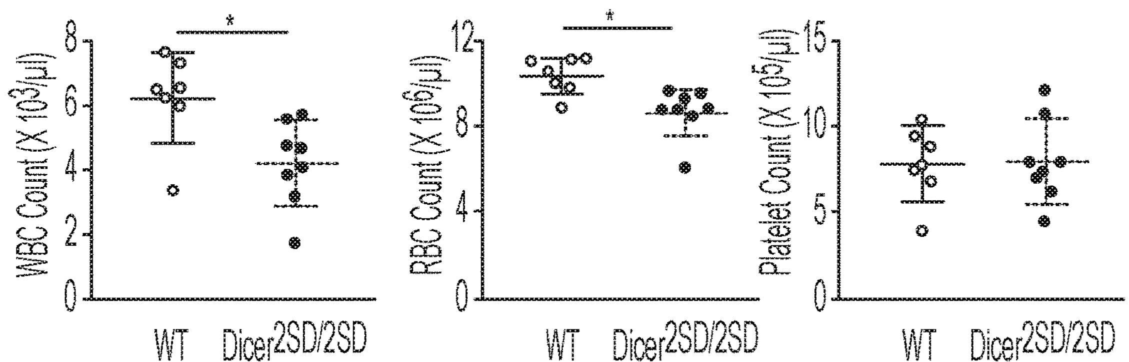

Constitutive Dicer1 phosphorylation at Serines 1712 and 1836 drives accelerated aging phenotype: Aging phenotypes in mice are assessed by several criteria including growth retardation, infertility, reduced survival, Kyphosis (curvature in the spine), osteoporosis, skin atrophy, cardiomyopathy, muscular dystrophy, reduced fat mass, anemia, and alopecia (Gurkar and Niedernhofer, 2015; Harkema et al., 2016; Koks et al., 2016; Reiling, et al., 2014; Treiber et al. 2011. As $Dicer^{2SD/2SD}$ mice display retarded growth, infertility and early lethality which suggests accelerated aging, other phenotypes of accelerated aging were examined in these mice. Examination of mutant and wild type mice as they aged revealed pronounced hunched posture in $Dicer^{2SD/2SD}$ mice starting at 6 months of age as compared with normal posture in wild type littermates (FIG. 6A). Quantitative Micro-computerized tomography (Micro-CT) scans of 7-9 month old $Dicer^{2SD/2SD}$ and wild type mice confirmed significant kyphosis in mutant mice relative to wild type mice (kyphosis index=2.5 and 3.7 respectively, p=0.02, FIGS. 6A and 6B). Micro-CT scans also revealed severe osteoporosis in $Dicer^{2SD/2SD}$ mice with significant reduction in bone volume fraction (38% vs 65%, p=0.0003, FIG. 6C) and bone mineral density (347 mg/cc vs 420 mg/cc, p=0.008, FIG. 6D) in the spine of mutant mice as compared with wild type mice. Histopathologic examination of the femur and tibia showed that the bone marrow was infiltrated by adipocytes in mutant mice as early as 2 months of age, and the adipocytes replaced most of the hematopoietic cells by 9 months (FIGS. 6E, 6F, and 6A). Bone loss was also observed throughout the skeletons of mutant mice (FIGS. 6A and 6E). As hematopoietic cells are predominantly found in the bone marrow in mice, the mutant animals were examined for compromised hematopoiesis. Complete blood count analysis revealed no change in platelet count (p=0.89), a 33% reduction in total white blood cell count (4.18 vs 6.22 $10^3/\mu L$, p=0.01) and 15% reduction in red blood cell count (8.6 vs 10.3 $10^6/\mu l$, p=0.007) in $Dicer^{2SD/2SD}$ mice as compared with wild type (FIG. 7B). These results suggest that phospho-mimetic Dicer1 dramatically impacts the skeletal integrity and bone marrow adipogenesis with an associated reduction of hematopoiesis.

Figure 7C:
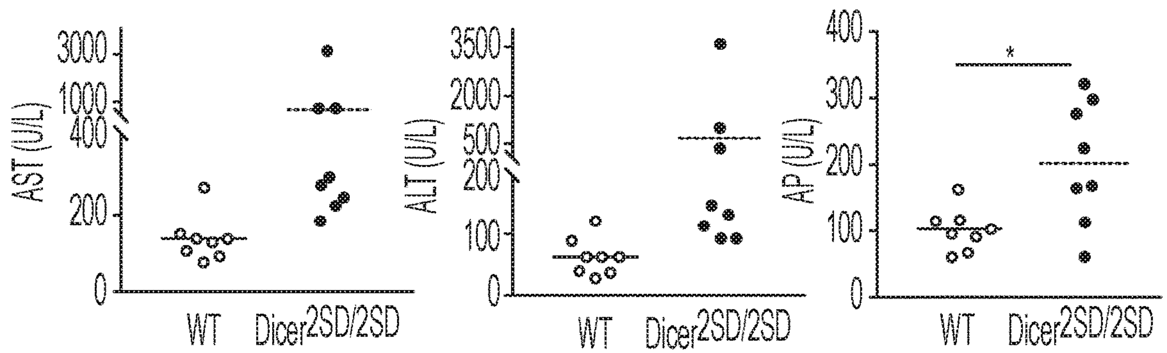

Multiple organs were examined from $Dicer^{2SD/2SD}$ and wild type mice microscopically to assay tissue degeneration. Consistent with the previous observation of infertility in the mutant mice, sections of testes from 2-7 month-old mutant mice lacked mature spermatozoa and had reduced numbers of leydig cells as compared with wild type mice (FIG. 6F). Similarly, the ovaries from homozygous mutant mice were reduced in size, contained fewer follicles and the majority of ovarian parenchyma was composed of vacuolated cells (FIG. 6F). The epidermis in mutant mice was thin with abnormal tissue architecture and reduced amounts of subcutaneous adipose tissue (FIG. 6F). Mutants over 6 months of age consistently lacked abdominal fat. Young $Dicer^{2SD/2SD}$ mice (1-2 month-old) also developed neutrophilic conjunctivitis, and as the mice aged, they occasionally developed corneal lesions. Additionally, reproductive tissues including the prostate, seminal vesicles, and uterus were reduced in size and the accessory sex glands contained less secretory material in mutants. Chronic cardiomyopathy, membrano-proliferative glomerulonephritis, hepatocellular karyomegaly, pulmonary bronchus-associated lymphoid tissue (BALT) hyperplasia was also observed in some mutant mice. The BALT hyperplasia and membrano-proliferative glomerulonephritis indicate non-specific chronic immune stimulation. Due to these lesions indicating chronic immune stimulation in multiple organs of $Dicer^{2SD/2SD}$ mice, it was suspected that the mutant mice might have altered serum enzymes in circulation. Blood chemistry analysis revealed elevated levels of aspartate aminotransferase (729 vs 136 U/L), alanine aminotransferase (703 vs 63 U/L), and alkaline phosphatase (202 vs 100 U/L) in mutant mice (FIG. 7C). All phenotypes present in $Dicer^{2SD/2SD}$ mice were also evident in $Dicer^{S1836D/S1836D}$ mice albeit with less severity. These results together suggest that phospho-mimetic Dicer1 disrupts normal tissue function resulting in infertility, tissue atrophy and changes often associated with aging including osteoporosis, reduced hematopoiesis, and increased bone marrow adipogenesis.

The end result of accelerated aging is shortened lifespan. While all $Dicer^{+/+}$ and $Dicer^{S1712D/S1712D}$ mice were alive by 540 day time point of this study, $Dicer^{2SD/2SD}$ and $Dicer^{S1836D/S1836D}$ mice had a median survival of 236 days and 302 days, respectively (p=0.0001, FIG. 6G). In line with previous observations that $Dicer^{2SD/2SD}$ mice display phenotypes with greater magnitude than $Dicer^{S1836D/S1836D}$ mice, the difference in overall survival between $Dicer^{S1836D/S1836D}$ and $Dicer^{2SD/2SD}$ mice was also statistically significant (p=0.02). Together, these results reveal that constitutive Dicer1 phospho-mimic at Ser1836, or dual phospho-mimic, drives accelerated aging phenotypes, and further supports the hypothesis that phosphorylation alters Dicer1 functions.

Figure 8A:
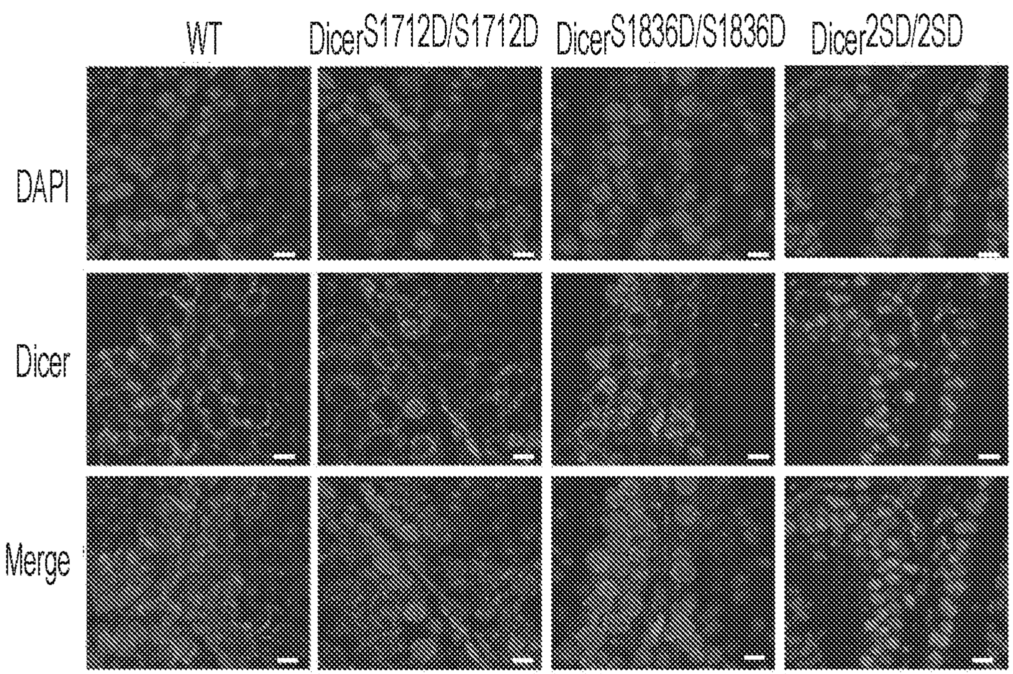
Figure 8B:
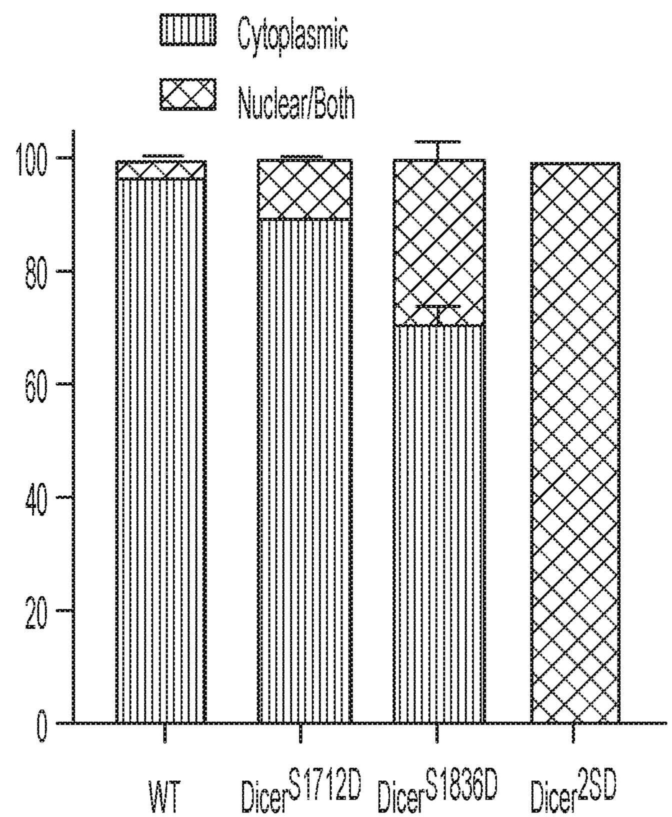

Phosphorylation alters Dicer1 localization: As phosphorylation leads to nuclear localization of Dicer1 in C. elegans, Dicer1 localization was examined in mutant and wild type testes. Immuno-fluorescence staining using a Dicer1 antibody on mouse testes sections from wild type and mutant mice revealed that Dicer1 protein accumulated in the nucleus in 3% of wild type, 10% of Dicer$^{S1712D/S1712D}$, 30% of Dicer$^{S1836D/S1836D}$, and 100% of Dicer$^{2SD/hu\ 2SD}$ spermatocytes that were positive for Dicer1 staining (FIGS. 8A and 8B). Using stringent criteria, spermatocytes with low levels of Dicer1 protein in the nucleus (<50% of nuclear surface) were considered negative for nuclear accumulation, and cells that were not stained with the Dicer1 antibody were excluded during quantification. Nuclear accumulation of Dicer$^{2SD/2SD}$ was also confirmed in kidney and liver sections. This result provided two insights. First, phosphorylation at both sites is essential for efficient nuclear translocation of Dicer1 protein. Second, phospho-mimetic mutation at Ser1836, with cytoplasmic Dicer1 protein in most cells, was sufficient to drive the observed phenotypes in mice. This suggests that phospho-mimic at Ser1836 is sufficient to impair Dicer1 functions, irrespective of the degree of nuclear localization.

Constitutive Dicer1 phosphorylation at Serines 1712 and 1836 alters a subset of metabolic miRNAs: To determine whether phosphorylation of Dicer1 at Serines 1712 and 1836 altered its canonical miRNA processing function, the mature miRNAs were identified using next generation deep sequencing in mouse embryonic fibroblasts (MEFs) and testes of wild type and Dicer$^{2SD/2SD}$ mice. MEFs were profiled to determine the earliest molecular changes before manifestation of gross pathologies. Testes were profiled because clear morphological changes were observed in this tissue as the animal aged.

Figure 8C:
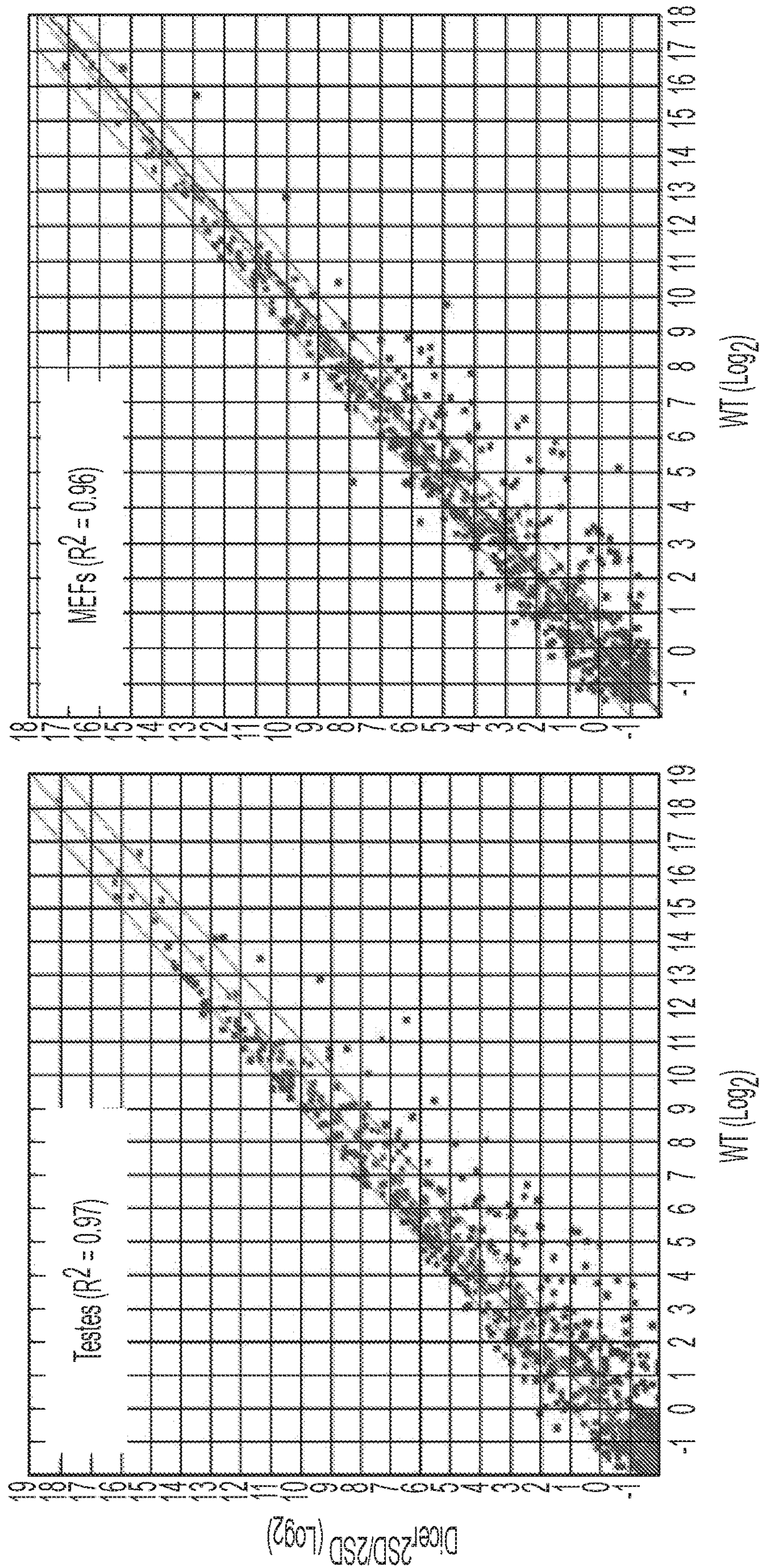

It was found that a subset of miRNAs were downregulated in both the MEFs and testes samples from Dicer$^{2SD/hu\ 2SD}$ mice as compared with wild type samples (FIG. 8C). Of the 359 and 368 miRNAs expressed in MEFs and testes respectively, 49 miRNAs in the mutant MEFs (14%) and 52 miRNAs in the mutant testes (14%) were downregulated more than two-fold (>eight-fold on average). Of the 49 downregulated miRNAs in mutant MEFs, only 17 miRNAs were expressed in testes and 16 of these 17 miRNAs (94%) were downregulated in both tissues (FIG. 8D). Similarly, of the 52 downregulated miRNAs in mutant testes, 39 were expressed in MEFs and 16 of these 39 miRNAs (41%) were downregulated in both tissues (FIG. 8D). This overlap strongly suggests that phospho-mimetic mutations in Dicer1 modulate the generation of a subset of miRNAs. Pathway analysis on the differentially downregulated miRNAs in mutant testes highlighted metabolic pathways as most affected (FIG. 8E). Pathway analysis on differentially downregulated miRNAs from MEFs also led to the identification of the metabolic pathways, further underscoring the specificity of dysregulated processing of the affected miRNAs. As aging is linked with altered metabolism; these results suggested that downregulation of metabolism-associated miRNAs may be the driving force behind the accelerated aging phenotypes in mutant mice (27, 28). This led to the investigation of whether dual phospho-mimetic Dicer1 mice have altered metabolism.

Constitutive Dicer1 phosphorylation at Serines 1712 and 1836 drives a hypermetabolic phenotype: The identification of downregulated miRNAs in Dicer$^{2SD/2SD}$ mutants as players in metabolic pathways suggested that metabolism may be altered in these mice. To determine whether metabolic changes may be underlying the accelerated aging phenotypes of Dicer$^{2SD/2SD}$ mutants, the Comprehensive Lab Animal Monitoring System (CLAMS) test was used to measure activity and rates of respiration in 3-4 month old mutant mice and wild type littermates. It was observed that the mutant mice had a significant increase (24%) in average oxygen consumption rate (OCR) relative to wild type mice (52.6 vs 42.3 ml/kg/min, p=0.04, FIGS. 9A and 9B). This difference was more pronounced during the light period when the mice typically rest (38% increase relative to wild type, 52.7 vs 38.1 ml/kg/min, p=0.02, FIG. 9B). Similar to the increase in respiration rates, the mutant mice displayed a 50% increase in wheel activity than wild type mice (10,555 vs 7,057 rotations), and the difference was 2.5-fold during the light period (4,605 vs 1,853 rotations, FIG. 9C). Together, these results indicate that Dicer$^{2SD/2SD}$ mice exhibit an increased metabolic rate and hyperactivity during the resting period relative to wild type mice.

To investigate whether metabolic changes precedes the phenotypic manifestation, mouse embryonic fibroblasts (MEFs) were assayed from mutant and wild type mice and their glycolytic and mitochondrial respiration rates were measured using the Seahorse Bioanalyzer. Consistent with the results from the CLAMS test, Dicer$^{2SD/2SD}$ MEFs displayed a statistically significant increase in oxygen consumption rate (118.7 vs 88.6 pmoles/min, p=0.02) and extra-cellular acidification rate (111.8 vs 84.4 mpH/min, p=0.04) as compared with wild type MEFs (FIGS. 9D and 9E). These results indicate that the increased metabolic rates are likely the earliest defects presented in Dicer$^{2SD/2SD}$ mice during embryonic development and influence the defects that manifest later. Taken together, these results demonstrated that phospho-mimetic Dicer1 regulates metabolic pathways and suggest that increased metabolic rates may be the underlying mechanism behind accelerated aging phenotypes of Dicer$^{2SD/2SD}$ mice.

The studies showed that phospho-mimetic Dicer1 affects a broader spectrum of tissues and phenotypes than have been previously described for Dicer1 hypomorphic alleles. These results demonstrate that phosphorylation is an important regulator of Dicer1 function in mammals, and phosphorylation mediated alteration in Dicer1 function and the associated phenotypes are different from Dicer1 null or hypomorphic alleles. Thus, dysregulation of Dicer1 phosphorylation may be associated with multiple human pathologies, and pharmacological intervention to control this process may have far reaching benefits.

Example 4—Materials and Methods

Construct design and generation of mouse models: The targeting construct was designed to generate a double phospho-mimetic mutant (S1712D and S1836D in the same allele), with possibilities to obtain single mutants. The construct contains a floxed neomycin-resistance gene (neoR) inserted into intron 24 of Dicer1 with 5.9 Kbp 5' homologous arm and 2.7 Kbp 3' homologous arm. The 5' arm contains S1712D mutation (TCT->GAT) while the 3' arm contains S1836D mutation (TCT->GAT). The S1712D mutation on the 5' arm divides the homologous region into 4.2 Kb outer region and 1.7 Kb inner region (considering neoR as the center). Similarly, the S1836D mutation divides the 3' arm into 2.0 Kb outer region and 0.7 Kb inner region. When homologous recombination (HR) occurs at the outer region of both homologous arms, both mutations will be introduced and a double mutant will be generated. On the other hand, if HR occurs at the outer region of one homologous arm (mutation is introduced) and inner region of the other homologous arm (mutation is not introduced), single mutants will be generated.

The construct was fully sequenced and successfully electroporated into TC1 mouse ES cells. Neomycin-resistant clones were screened by Southern blot analysis using 5' and 3' external probes. SpeI-digested genomic DNA was used for southern blot screening. Positive clones were confirmed by PCR and sequencing of targeted region. Two lines of ES clones that were accurately generated were injected into blastocysts which were then implanted into pseudo-pregnant females to generate chimeras. Male chimeras were crossed to C57BL/6 females for germline transmission of the mutant allele. One male progeny carrying the mutant allele was crossed with C57BL/6 female mice carrying Zp3-Cre transgene to remove the neomycin resistance gene. Male progeny carrying the mutant allele (without neoR) was crossed with wild type C57BL/6 females for 2 more generations.

CRISPR/Cas9 based gene targeting: As previously described (Aryal et al., 2017), a target site was selected, sgRNA was synthesized, and fertilized zygotes were injected with sgRNA, Cas9 mRNA, and donor oligo containing the mutation. Briefly, a 43-base sequence (20 bases on either side of the targeted codon) was used to score all possible target sites using the crispr.mit.edu tool. A site with high score and containing the mutagenesis site in the seed region of sgRNA was selected for targeting. Six possible off-target sites with a PAM sequence were also selected for screening unintended mutations.

The template for sgRNA synthesis was generated by annealing two complementary oligo-nucleotides (sequence listed below). The T7 promoter sequence is underlined, and sgRNA target sites are in bold.

(SEQ ID NO: 17)
5'GAAATTAATACGACTCACTATAGACCCACGGCAGCATTCTCC
GTTTTAGAGCTAGAAATAGCAAGTTAAAATAAGGCTAGTCCGTT
ATCAACTTGAAAAAGTGGCACCGAGTCGGTGCTTTT3'

5 μg of both oligos were mixed in nuclease-free water, boiled for 5-10 minutes and cooled at room temperature for 2 hrs to overnight. 200-400 ng of the template was used to synthesize sgRNAs using the MEGAshortscript Kit (Invitrogen AM1354), sgRNAs were purified by acid phenol-chloroform extraction and ethanol precipitation (Invitrogen), re-suspended in 70 μl of RNase-free water and further purified by using Biospin P30 chromatography columns (#732-6223, Biorad) as per manufacturer's protocol. A final injection solution containing 10 ng/μl Cas9 mRNA (PrecisionX hspCas9 SmartNuclease mRNA, System Biosciences), 7.5 ng/μl of sgRNA, and 20 ng/μl of donor oligo was prepared in Tris-EDTA buffer (5 mM Tris, 0.1 mM EDTA). The final solution was injected into the pronucleus of 200-250 zygotes. The zygotes were then implanted into pseudo-pregnant mice (20-25 per animal). All injections and implantations were done in the MD Anderson genetically engineered mouse facility.

Selection and screening of off-target sites: List of all possible off-target sites were obtained from crispr.mit.edu site. Previously described criteria (Aryal et al., 2017) were used to select the sites for screening. Primers are designed about 500 bases upstream and 500 bases downstream of the selected sites, and the region is PCR amplified and sanger-sequenced.

OTS1 Fwd: (SEQ ID NO: 18)
GCTCAGTGGCTGGCATATATG

OTS1 Rev: (SEQ ID NO: 19)
CCCAACTGCAGCTCCTTTG

OTS2 Fwd: (SEQ ID NO: 20)
GCCGTGATTTGGGACAAAAAG

OTS2 Rev: (SEQ ID NO: 21)
CCCCATAGGTGGGTTTGTATC

OTS3 Fwd: (SEQ ID NO: 22)
CCCCCATAGCTGGTTCAAAC

OTS3 Rev: (SEQ ID NO: 23)
GGCAACAAGGGCAGATACATG

OTS4 Fwd: (SEQ ID NO: 24)
CCTCTAGGCCTGTGATCAGAATAG

OTS4 Rev: (SEQ ID NO: 25)
GGCGGGTTAATGACTCATACAG

OTS5 Fwd: (SEQ ID NO: 26)
GGCTGGACATAGTTGTCTGTTG

OTS5 Rev: (SEQ ID NO: 27)
GCTCCACCTGGCTTCATTATC

OTS6 Fwd: (SEQ ID NO: 28)
GAGGACCGATGGTTGTGAAAAATC

OTS6 Rev: (SEQ ID NO: 29)
CCTGGCACCTAGGAGAATTTAG

Mouse breeding, maintenance, screening and genotyping: Mice were maintained in >90% C57BL/6 background. All mouse studies were conducted in compliance with an Institutional Animal Care and Use Committee protocol. Live mice were weaned at the age of three weeks, and ear biopsies were collected. The tissues were digested by Lysis buffer (1×PCR buffer, 1% Triton X, 250 μg/μL Proteinase K) at 55° C. overnight, and heated at 95° C. for 15 minutes to denature Proteinase K. 2 μL of the lysed tissue extract was used for PCR reaction to amplify 1 Kb region of the targeted site. The PCR product is gel purified and sanger-sequenced to identify any indels at the target site.

S1712D screening primer Fwd: (SEQ ID NO: 30)
GTGCCAGGGATGTAGAAGAC

S1712D screening primer Rev: (SEQ ID NO: 31)
GGGCTGCAGGAATTCGATATC

-continued

```
S1836D screening primer Fwd:
                              (SEQ ID NO: 32)
CACGTGGTACCTTAAGATGCATG

S1836D screening primer Rev:
                              (SEQ ID NO: 33)
GCGGGTGACTTGAACCTAAG
```

Homozygous Viability Test: For each mutant allele, heterozygous mice were inbred and the progeny were genotyped at weaning. From five Dicer$^{+/S1712D}$ mating pairs, ten litters with a total of 85 progeny were genotyped at weaning. From four Dicer$^{+/\Delta1712}$ mating pairs, eight litters with a total of 68 progeny were genotyped at weaning. From three Dicer$^{+/-}$ mating pairs, five litters with a total of 28 progeny were genotyped at weaning. From seven Dicer$^{+/S1836D}$ mating pairs, fourteen litters with a total of 103 progeny were genotyped at weaning. From ten Dicer$^{+/2SD}$ mating pairs, eighteen litters with a total of 115 progeny were genotyped at weaning.

E18.5 embryo Dissection: Dicer$^{+/2SD}$ and Dicer$^{+/S1836D}$ heterozygous animals were inbred, and plugs were examined every morning. Females positive for plug (E0.5) were euthanized 18 days from that date (E18.5). Uteri were dissected, and each decidua is separated and placed in a 10 cm plate with PBS buffer. Each decidua is dissected to recover the embryos. Embryos were examined for viability, weighed, euthanized, and tail biopsies were collected and genotyped.

Weight measurements: Weaned wild type (12 males and 12 females), Dicer$^{S1836D/S1836D}$ (12 males and 9 females), and Dicer$^{2SD/2SD}$ (10 males and 11 females) were weighed (to tenth of a gram) every week from four weeks after birth by using an electronic scale. When a mutant mouse was euthanized, its littermate wild type mouse was also sacrificed. At least 3 mice were present at all time points (both males and females) from all genotypes. An end point of ten months was selected because only 2 Dicer$^{2SD/2SD}$ mice (one male and one female) survived past this age.

Fertility Test: 8-12 week old homozygous mice (males and females) of all mutant alleles were mated with wild type mice (8-16 weeks old). The mating pairs were monitored daily and maintained until 1-2 litters were born. Litter size was counted and recorded at the time of weaning. In the absence of any progeny, wild type animals were replaced with younger (8-16 weeks old) wild type mice every two months for 6 months.

Micro-CT Scan: Micro-CT scans were performed at the small animal imaging facility of MD Anderson Cancer Center. Briefly, four Dicer$^{2SD/2SD}$ mice (two males and two females, 6-8 months old) and their four wild type littermates (two males and two females) were anesthetized using isoflurane, immobilized, and scanned using the Explore Locus RS pre-clinical in-vivo scanner (GE Medical Systems) which is a cone-beam volume CT system that permits live imaging of rodents. The X-ray source and CCD-based detector gantry is rotated around the subject in roughly 1.0-degree increments. Geometric models were produced by the system. Micro View software was used to create isosurface with threshold of 700 (Th700) and 1000 (Th1000). Quantifications of bone mineral densities (BMD) and bone volume fractions (BVF) of spine were done at Th700. Kyphosis index was calculated as previously described (Laws and Hoey, 2004).

Histopathology and immuno-fluorescence staining: As previously described, tissues harvested from mice were fixed in 10% neutral buffered formalin and paraffin-embedded. Four micrometer sections were stained with hematoxylin and eosin (H&E), and examined by light microscopy. Tissue processing, paraffin embedding, sectioning, and H&E staining were performed by the MD Anderson Department of Veterinary Medicine & Surgery Histology Laboratory. Selected unstained sections were analyzed by immunofluorescence with respective antibodies. Total-Dicer1 antibody (1:30, MABN461, EMD Millipore) and phospho-Dicer specific antibody (1:100, [Drake, et al., 2014]) were used). Quantification of cells with nuclear Dicer1 in testes sections was performed manually. Tissue sections stained with total-Dicer1 antibody and DAPI were used. Three 20× images (different regions) of each testis section (three testes sections from wild type, Dicer$^{S1712D/S1712D}$, Dicer$^{S1836D/S1836D}$ and Dice?SD/2SD mice) were taken. Images were opened using ImageJ software, and total number of spermatocytes (round nuclear staining by DAPI, spermatids and spermatozoa were excluded) were counted per seminiferous tubule. Cells with Dicer1 staining in >50% of nucleus were considered positive for nuclear staining. To avoid bias, a blinded-study was performed.

Survival Curve: A cohort of Dicer$^{S1712D/S1712D}$ (n=15), Dicer$^{S1836D/S1836D}$ (n=21), Dicer$^{2SD/2SD}$ (n=21) and wild type (n=57) littermate mice was generated and monitored every day after weaning (three weeks after birth). Moribund animals were euthanized and their tissues were harvested. When the mutant mice were euthanized, the littermate control mice were also euthanized. Mice that had to be euthanized for non-moribund reasons were excluded from the study.

MEF preparation and cell culture: Dicer$^{+/2SD}$ heterozygous animals were inbred and plugs were examined every morning. Females positive for plug (E0.5) were euthanized 13 days from that date (E13.5). Uteri were dissected, and each decidua is separated and placed in a 10 cm plate with PBS buffer. Each decidua is dissected to recover the embryos. Fetal liver, head and limbs (collected for genotyping) were removed from each embryo, and the remaining tissues were chopped and treated with trypsin for 5-10 minutes at 37° C. 5 mL of DMEM media supplemented with 10% FBS and penicillin/streptomycin was added to each sample, and the cells were dissociated by pipetting up and down. Cells were centrifuged, washed with PBS, re-suspended in 10 mL media, transferred to 10 cm plates, and incubated at 37° C. Media was changed every 24 hours, and the cells were harvested and re-plated (into 3-4 plates) when they reached confluency. Early passage MEFs (P2-P3) were used for analysis.

Small RNAseq and Pathway Analysis: RNA from testes and MEFs were extracted and purified per manufacturer's protocol (Direct-zol RNA Miniprep plus, ZYMOL) and submitted to the M.D. Anderson sequencing core facility. Barcoded libraries were prepared using the Illumina TruSeq small RNA seq Kit. The libraries were sequenced on the NextSeq500. Quality assessment of the Illumina raw reads was performed with FASTQC.

1915 mature miRNA sequences from the mouse genome assembly GRCm38 were obtained from the miRBase and used as reference for subsequent short read mapping (Kozomara and Griffiths-Jones, 2014). Contaminating adapter sequences were removed using the adapter scan function implemented in SeqMan NGen® version 14 (DNASTAR, Inc, Madison, WI). Sequences with median quality lower than phred=30 were discarded from the analysis. Short read mapping to reference mature miRNAs was also performed with SeqMan NGen® with the following specifications: mer size (the minimum length of a mer, overlapping region of a fragment read, in bases, required to be considered a match when assembling reads into contigs)=15; minimum match percentage (specifies the minimum percentage of matches in an overlap that are required to join two sequences in a contig)=95%; and minimum aligned length (the minimum length of at least one aligned segment of a read after trimming)=18. Duplicate sequences were marked and combined.

Statistical analysis of mapped data from technical and biological replicates was performed with ArrayStar® (DNASTAR Inc., Madison, WI). Briefly, normalization of mapped data was done using the RPM method, and fold change in miRNA abundance between the wild type and mutant samples was calculated from log 2 of total RPM (51). Significance of observed differences was determined with the Student's t-test and the Benjamini-Hochberg correction was employed for multiple hypothesis testing; false discovery rate (FDR) was set at 0.05. Hierarchical clustering was performed with the Euclidean distance.

Finally, all miRNAs with less than 10 reads/million in both groups (wild type and mutant) were filtered out. Differentially expressed miRNAs with less than 2 fold difference and confidence interval of <95% were filtered out. From the final list, pathway analysis on differentially expressed miRNAs was performed using DIANATOOLS mirPath V.3 software. List of miRNAs were uploaded into the program, and analysis was performed using three different target prediction tools (TarBase, Targetscan and, microT-CDS).

CLAMS Test: Briefly, four Dicer$^{2SD/2SD}$ mice (two males and two females) and two wild type mice (one male and one female) were housed in individual metabolic cages, acclimatized for two hours, and measurements were made every minute for 24 hours. The calorimetry system monitored oxygen consumption rate and carbon dioxide production rate. The free running wheels in each cage recorded the number of revolutions and the time of day when the activity occurred. The CLAMS system also monitored the amount of food consumed by the mouse, and the frequency and duration of each meal. All animals were weighed at the beginning and end of the experiments.

Seahorse Metabolic assays: As per manufacturer's protocol (Seahorse Bioscience, XFe96 training manual), passage two Dicer$^{2SD/2SD}$ (n=3) and wild type (n=2) MEFs were trypsinized, counted, and re-suspended to a concentration of 200 cells/µl in DMEM media supplemented with 10% FBS and penicillin/streptomycin. 80 µl of each MEF samples (6 technical replicates) were plated into a 96-well plate and incubated at 37° C. overnight. Sensor cartridge was hydrated with XF calibrant overnight at 37° C. Next day, the cells were washed and incubated with assay-specific media (described in manual) for one hour at 37° C. in a non-CO2 incubator. Sensor cartridge was loaded into the machine for pre-calibration, and the plate with cells are loaded when ready. Measurements (oxygen consumption rate and extra cellular acidification rate) were made 3-5 times. The experiment was repeated with new Dicer$^{2SD/2SD}$ (n=6) and wild type (n=5) MEFs. For data analysis, average of technical replicates were used and the two experiments were combined.

Statistical analysis: Student's t-tests and Kaplan-Meier survival analyses were performed using Prism 7 Software (GraphPad Software). P-values <0.05 were considered statistically significant.

Example 5-Phosphorylated Human Monoclonal DICER1 Antibody as a Biomarker for Invasive Human Cancers Studies were performed to determine whether the human monoclonal anti-phosphorylated Dicer1 antibody detects Dicer1 in human cancer cells. Papillary thyroid carcinoma cells with BRAF600E mutations were stained with anti-phosphorylated monoclonal Dicer1 antibody against S1852 used at 1:200. Secondary antibody anti-mouse 488 used at 1:500. These studies confirmed that phosphorylated Dicer1 is nuclear in thyroid carcinoma cells.

To determine whether Dicer1 in phosphorylated in cancers, the monoclonal antibody was used on endometrial cancers with KRAS and FGF oncogenic mutations and no mutations in POLE2 or Dicer1. 58 tumors were assayed with increasing grade of disease with a tissue microarray. It was found that as the grade of the tumor increases Dicer1 is phosphorylated and has nuclear localization in the endometrioid endometrial cancers. Phosphorylated Dicer1 is positive and nuclear in Grade 1 endometrioid endometrial cancers, but was found to an even greater extent in Grade 3-4 endometrioid endometrial cancers.

Figure 10:
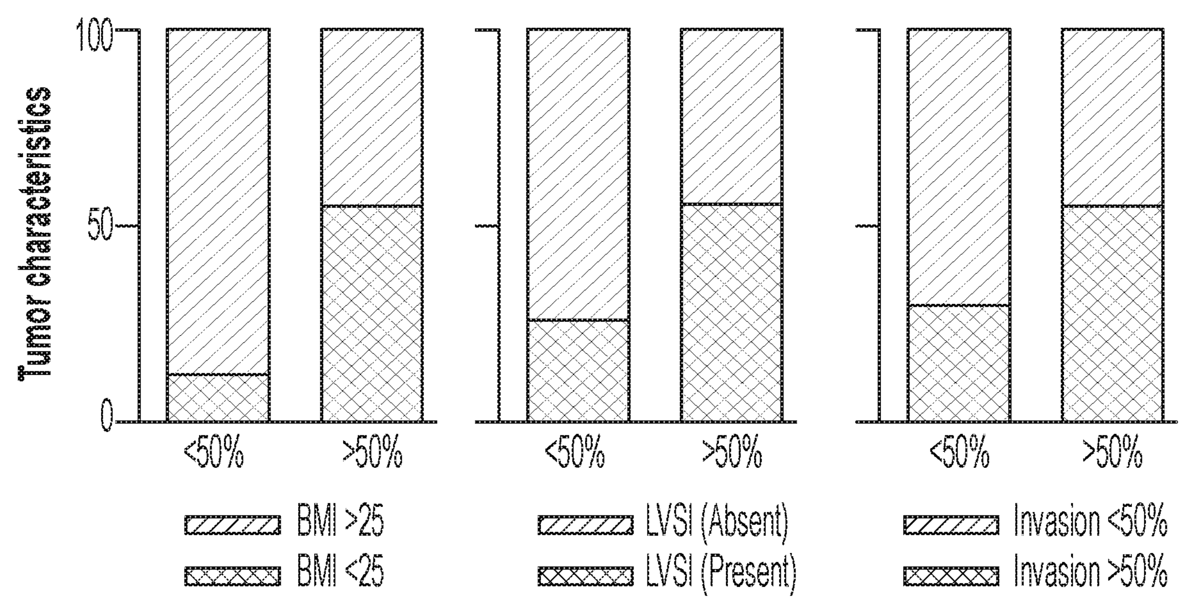
FIG. 10: Tumor characteristics of 54 endometroid endometrial cancers tested on tissue microarray. Each tumor was classified as either less than 50% of phosphor-Dicer1 positive cells, or more than 50%.

Of the 54 endometrioid endometrial cancers tested on the tissue microarray with the anti-phosphorylated Dicer1 monoclonal antibody, 84% of tumors were positive for phospho-Dicer1. To determine whether there was any relationship between pDICER1 expression levels in the tumors and clinicopathologic features of the endometrioid endometrial cancer, each tumor was classified as either less than 50% of pDicer1 positive cells, or more than 50% (FIG. 10). Those with less than 50% were grouped as "low-to-moderate" for Dicer1 phosphorylation (n=35), and tumors with over 50% of cells with phospho-Dicer1 were grouped as "high" for Dicer1 (n=16).

High pDicer1 was associated with lower body mass index (p=0.002) and deep myometrial invasion (p=0.03) (FIG. 10, Table 2). In addition, there was also a trend wherein the presence of lymphvascular space invasion (p=0.06) was higher in tumors with high pDicer1. Deep myometrial invasion and increased lympho-vascular space invasion is a feature of poor outcome in these cancers. Together, these data indicate that the presence of nuclear pDicer1 correlates with endometrial tumor invasion.

TABLE 2

Associated between tumor nuclear DICER1 status and demographic and clinicopathologic variables.

Table 1. Association between tumor nuclear DICER1 status and demographic and clinicopathologic variables.

| | Nuclear DICER1 Positivity | | | |
|---|---|---|---|---|
| Clinicopathologic Factor | Low N (%) | Medium N (%) | High N (%) | p value* |
| Age | | | | |
| <60 years | 5 | 10 | 7 | 0.10 |
| ≥60 years | 14 | 6 | 9 | |
| BMI | | | | |
| <25 (normal or underweight) | 2 | 2 | 8 | <0.01 |
| ≥25-30 (overweight) | 16 | 14 | 6 | |
| Grade | | | | |
| 1 | 9 | 9 | 9 | 0.80 |
| 2 | 3 | 3 | 1 | |
| 3 | 7 | 4 | 6 | |

TABLE 2-continued

Associated between tumor nuclear DICER1 status and demographic and clinicopathologic variables.

Table 1. Association between tumor nuclear DICER1 status and demographic and clinicopathologic variables.

| Clinicopathologic Factor | Nuclear DICER1 Positivity Low N (%) | Medium N (%) | High N (%) | p value* |
|---|---|---|---|---|
| Stage | | | | |
| I or II | 12 | 11 | 8 | 0.54 |
| III or IV | 7 | 5 | 8 | |
| LVSI | | | | |
| Present | 7 | 2 | 9 | 0.03 |
| Absent | 12 | 14 | 7 | |
| Depth of invasion | | | | |
| <50% | 10 | 13 | 5 | 0.02 |
| ≥50% | 9 | 3 | 11 | |

*Fisher's exact test
BMI (body mass index) data missing for 3 cases.
LVSI (lymphvascular space invasion)

Since phosphorylated Dicer1 can mark invasive cancers, it can be used for stratifying patients with different grades of the disease for treatment. Thus, the next studies assayed a different tumor type which was driven by BRAF oncogenic mutations rather than KRAS. BRAF600E positive metastatic melanoma cancers were assayed. Phosphorylated DICER1 expression in melanoma and benign nevi samples was measured in a tumor microarray. Four separate measurements were provided including nuclear intensity, nuclear percentage, cytoplasmic intensity, and cytoplasmic percentage. There were four separate types of tissue analyzed including primary tumor without metastasis, primary tumor with metastasis, metastatic, and nevus (benign).

The association between phosphorylated DICER1 expression and survival was assessed using Cox proportional hazards regression models. Two measurements of survival were considered including overall survival and disease-free survival. Analyses were performed separately within each of the four tissue types. Phosphorylated DICER1 expression was compared between the tissue types using t-tests. Three comparisons were of interest including primary tumor with metastasis vs. primary tumor without metastasis, combined primary tumor with and without metastasis plus metastatic vs. benign nevi, and combined primary tumor with and without metastasis vs. metastatic. Similar analyses were performed to compare ulceration with no ulceration, VGP with no VGP, and vascular invasion with no vascular invasion. Spearman rank correlation analysis was used to assess the association between the continuous parameters Clark level, Breslow thickness, age, and tumor regression and the DICER expression levels. No formal adjustment was made for the multiplicity of testing.

Association between phosphorylated DICER1 expression and survival: The association between phosphorylated DICER1 expression and both overall and recurrence-free survival was assessed using Cox proportional hazards regression analysis. Table 3 presents results for overall survival. The hazard ratio and corresponding 95% confidence interval are presented, along with a p-value for the test of the hypothesis of association. OS correlated with pDICER1 nuclear intensity and percentage for metastatic disease. However, for primary samples with metastasis, all of the cytoplasmic intensity measurements were 0 for patients who died, and therefore a survival model could not be fit. A Wilcoxon rank-sum test was performed to assess whether cytoplasmic intensity expression levels were different in patients who died than in patients who survived; the comparison is statistically significant (p=0.017).

TABLE 3

Results for overall survival analysis.

| Diagnosis Type | Parameter | Hazard Ratio | HR: 95% CI | P-Value |
|---|---|---|---|---|
| Primary without Metastasis | Nuclear Intensity | 0.45 | 0.62, 1.63 | 0.0022 |
| | Nuclear Percentage | 0.98 | 0.95, 1.02 | 0.0032 |
| | Cytoplasmic Intensity | 0.07 | 0.35, 2.68 | 0.0095 |
| | Cytoplasmic Percentage | 0.01 | 0.95, 1.05 | 0.0098 |
| Primary with Metastasis | Nuclear Intensity | 0.93 | 0.41, 4.15 | 0.92 |
| | Nuclear Percentage | 0.99 | 0.95, 1.03 | 0.60 |
| | Cytoplasmic Intensity | * | * | * |
| | Cytoplasmic Percentage | 0.03 | 0.07, 1.04 | 0.96 |
| Benign Nevus | Nuclear Intensity | 0.08 | 0.21, 14.2 | 0.60 |
| | Nuclear Percentage | 0.1 | 0.14. 1.09 | 0.76 |
| | Cytoplasmic Intensity | 0.72 | 0.95, 2.12 | 0.55 |
| | Cytoplasmic Percentage | 0.99 | 0.97, 1.02 | 0.56 |

Association between pDICER1 Expression and Tissue Type: Phosphorylated DICER1 expression levels were compared between groups using t-tests. Table 4 presents results for the comparison of primary samples without metastasis and primary samples with metastasis. The table presents the mean and standard deviation (SD) for each group, along with the number of samples and a p-value for a t-test. There is evidence of differences in nuclear intensity of phosphorylated DICER levels between the two groups.

TABLE 4

Primary without metastasis vs. primary with metastasis.

| Parameter | Primary w/o Mets Mean (SD) | N | Primary w/Mets Mean (SD) | N | P-Value |
|---|---|---|---|---|---|
| Nuclear Intensity | 0.63 (0.77) | 38 | 5.56 (0.62) | 27 | 0.07 |
| Nuclear Percentage | 13.7 (28.3) | 38 | 0.20 (24.6) | 27 | 0.02 |
| Cytoplasmic Intensity | 1.22 (0.85) | 38 | 1.33 (0.56) | 27 | 0.53 |
| Cytoplasmic Percentage | 48.7 (19.2) | 38 | 53.0 (16.5) | 27 | 0.52 |

Table 5 presents results for the comparison of all melanoma samples (primary plus metastatic) vs. benign nevi. There is substantial evidence of differences in phosphorylated DICER levels between the two groups for nuclear intensity and percentage, with higher levels found in melanoma samples. There is no evidence of a difference in levels between melanoma and nevi for cytoplasmic intensity and percentage.

TABLE 5

All melanoma (combined primary with and without metastasis plus metastasis) vs. benign nevi.

| Parameter | Combined Melanoma Mean (SD) | N | Nevi Mean (SD) | N | P-Value |
|---|---|---|---|---|---|
| Nuclear Intensity | 7.5 (0.68) | 99 | 41.2 (38.5) | 17 | 0.003 |
| Nuclear Percentage | 0.34 (28.4) | 99 | 1.00 (0.94) | 17 | 0.01 |

TABLE 5-continued

All melanoma (combined primary with and without metastasis plus metastasis) vs. benign nevi.

| | Combined Melanoma | | Nevi | | |
|---|---|---|---|---|---|
| Parameter | Mean (SD) | N | Mean (SD) | N | P-Value |
| Cytoplasmic Intensity | 55.3 (0.69) | 99 | 60.9 (24.4) | 17 | 0.4 |
| Cytoplasmic Percentage | 1.38 (15.9) | 99 | 1.21 (0.53) | 17 | 0.25 |

Table 6 presents results for the comparison of all primary melanoma samples (with and without metastasis) and metastatic samples. Phosphorylated DICER1 levels for nuclear intensity and percentage are significantly lower in primary samples than in metastases, while cytoplasmic intensity and percentage are substantially higher in primary samples than in metastases.

TABLE 6

Combined primary vs. metastases.

| | Combined Primary | | Metastases | | |
|---|---|---|---|---|---|
| Parameter | Mean (SD) | N | Mean (SD) | N | P-Value |
| Nuclear Intensity | 1.27 (0.71) | 65 | 1.59 (0.57) | 34 | 0.02 |
| Nuclear Percentage | 50.5 (26.7) | 65 | 64.4 (29.5) | 34 | 0.02 |
| Cytoplasmic Intensity | 0.45 (0.77) | 65 | 0.12 (0.41) | 34 | 0.006 |
| Cytoplasmic Percentage | 10.3 (18.5) | 65 | 2.06 (6.87) | 34 | 0.002 |

Table 7 provides details on the association between ulceration and pDICER1 expression levels for each of the four parameters. The mean, SD and N are provided for each group (ulceration and no ulceration) along with a p-value from a t-test. Nuclear percentage is significantly higher in ulcerated samples than in non-ulcerated ones.

TABLE 7

Association between ulceration and phosphorylated DICER1 expression.

| | Ulceration | | No Ulceration | | |
|---|---|---|---|---|---|
| Parameter | Mean (SD) | N | Mean (SD) | N | P-Value |
| Nuclear Intensity | 1.44 (0.58) | 17 | 1.16 (0.75) | 41 | 0.13 |
| Nuclear Percentage | 64.1 (21.2) | 17 | 44.8 (28.2) | 41 | 0.007 |
| Cytoplasmic Intensity | 0.29 (0.69) | 17 | 0.59 (0.84) | 41 | 0.18 |
| Cytoplasmic Percentage | 8.24 (20.4) | 17 | 12.4 (18.8) | 41 | 0.47 |

Table 8 summarizes the association between vascular invasion and pDICER1 expression levels. Cytoplasmic intensity and percentage are substantially higher in patients with no vascular invasion. There is no evidence that nuclear intensity or percentage is associated with vascular invasion. There are only 8 patients with vascular invasion.

TABLE 8

Associated between vascular invasion and DICER expression.

| | Vascular Invasion | | No Vascular Invasion | | |
|---|---|---|---|---|---|
| Parameter | Mean (SD) | N | Mean (SD) | N | P-Value |
| Nuclear Intensity | 1.19 (0.65) | 8 | 1.24 (0.74) | 49 | 0.83 |
| Nuclear Percentage | 40.0 (23.3) | 8 | 51.6 (28.4) | 49 | 0.23 |
| Cytoplasmic Intensity | 0 (0) | 8 | 0.56 (0.84) | 49 | <0.0001 |
| Cytoplasmic Percentage | 0 (0) | 8 | 13.1 (20.3) | 49 | <0.0001 |

Table 9 summarizes the association between VGP and DICER expression levels. There is mild evidence that nuclear intensity is higher in VGP patients.

TABLE 9

Associated between vertical growth phase (VGP) and DICER expression.

| | VGP | | No VGP | | |
|---|---|---|---|---|---|
| Parameter | Mean (SD) | N | Mean (SD) | N | P-Value |
| Nuclear Intensity | 1.34 (0.73) | 45 | 0.72 (0.57) | 9 | 0.01 |
| Nuclear Percentage | 52.6 (27.9) | 45 | 36.7 (29.6) | 9 | 0.17 |
| Cytoplasmic Intensity | 0.44 (0.76) | 45 | 0.89 (1.05) | 9 | 0.26 |
| Cytoplasmic Percentage | 10.2 (18.9) | 45 | 18.9 (23.2) | 9 | 0.32 |

There was only one patient in the perineural category, and thus analyses of the association between pDICER1 expression levels and the perineural variable were not performed.

Phosphorylated DICER1 monoclonal antibody when injected into the cell serves to neutralize phosphorylation and block its action. HEK293 cells (passage 5) were seeded at the density of $3\times10^5$ cells/well of the 6-well plates the day before the transfection. Phosphorylated DICER1 was visualized upon treatment with 200 ng of FGF2 for 30 minutes (see Drake et al., Developmental Cell, 2014). Phosphorylated DICER1 was nuclear in these cells. Phosphorylated DICER1 is nuclear upon FGF treatment in HEK293 cells.

To inject the anti-phosphorylated DICER1 antibody into the HEK293 cells after FGF incubation, 2×6-well plates of the cells were used. The parameters included HEK293 cells, with no FGF incubation, no anti-phospho-DICER1 antibody injection; HEK293 cells, plus FGF, no anti-phospho-DICER1 antibody injection; and HEK293 cells, plus FGF, plus anti-phospho-DICER1 antibody injection. As these are labor intensive experiments, only one plate of cells was injected for each experiment.

After FGF treatment and either mock injection or injection with anti-phospho-DICER1 antibody, the cells were stained with DAPI to mark nuclei and anti-caspase 3 antibody stain to assay for cell death. Due to a low number of injected cells, no statistical analysis was performed. Of the 10 cells injected for each treatment with either GFP antibody or anti-phosphorylated DICER1 antibody, in the anti-phosphorylated DICER1 treatment group, 8 out of 10 cells were positive for anti-caspase 3 while 0 out of 10 cells were positive for anti-caspase 3 in the control group. Thus, phosphorylated DICER1 antibody can be used to block DICER1 phosphorylation and function.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application No. 2004/0126828
U.S. Patent Application No. 2002/0172677
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,770,376
U.S. Pat. No. 5,789,208
U.S. Pat. No. 5,821,337
U.S. Pat. No. 5,844,091
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546

Aryal et al., Loss of digestive organ expansion factor (Diexf) reveals an essential role during murine embryonic development that is independent of p53. *Oncotarget* 8 (61): 103996-104006, 2017.

Bernstein et al., Dicer is essential for mouse development. *Nat Genet* 35 (3): 215-217, 2003.

Billingsley et al., *Polymerase varepsilon* (*POLE*) *mutations in endometrial cancer: clinical outcomes and implications for Lynch syndrome testing*. Cancer, 121 (3): p. 386-94, 2015.

Burger K, et al. (2017) Nuclear phosphorylated Dicer processes double-stranded RNA in response to DNA damage. *J Cell Biol* 216 (8): 2373-2389.

Burger, et al., Nuclear phosphorylated Dicer processes double-stranded RNA in response to DNA damage. *J Cell Biol* 216 (8): 2373-2389, 2017.

Drake et al., A requirement for ERK-dependent Dicer phosphorylation in coordinating oocyte-to-embryo transition in C. elegans. *Dev Cell,* 31 (5): p. 614-28, 2014.

Drake, et al., A requirement for ERK-dependent Dicer phosphorylation in coordinating oocyte-to-embryo transition in C. elegans. *Dev Cell* 31 (5): 614-628, 2014.

Drake, et al., A requirement for ERK-dependent Dicer phosphorylation in coordinating oocyte-to-embryo transition in C. elegans. *Dev Cell* 31 (5): 614-628, 2014.

Fedor and De Marzo, Practical methods for tissue microarray construction. *Methods Mol Med,* 2005. 103: p. 89-101, 2005.

Gurkar and Niedernhofer, Comparison of mice with accelerated aging caused by distinct mechanisms. *Exp Gerontol* 68:43-50, 2015.

Harkema et al., Pathology of Mouse Models of Accelerated Aging. *Vet Pathol* 53 (2): 366-389, 2016.

Hill et al., *DICER*1 *mutations in familial pleuropulmonary blastoma*. Science, 325 (5943): p. 965, 2009.

Jacks, et al., Tumor spectrum analysis in p53-mutant mice. *Curr Biol,* 4 (1): p. 1-7, 1994.

Johnson et al., Somatic activation of the K-ras oncogene causes early onset lung cancer in mice. Nature, 410 (6832): p. 1111-6, 2001.

Koks et al., Mouse models of ageing and their relevance to disease. *Mech Ageing Dev* 160:41-53, 2016.

Kozomara and Griffiths-Jones, miRBase: annotating high confidence microRNAs using deep sequencing data. *Nucleic Acids Res* 42 (Database issue): D68-73, 2014.

Kumar et al., Dicer1 functions as a haploinsufficient tumor suppressor. *Genes Dev,* 23 (23): p. 2700-4, 2009.

Laws and Hoey, Progression of kyphosis in mdx mice. *J Appl Physiol* (1985) 97 (5): 1970-1977, 2004.

Mudhasani et al., Loss of miRNA biogenesis induces p19Arf-p53 signaling and senescence in primary cells. *J Cell Biol* 181 (7): 1055-1063, 2008.

Pugh et al., Exome sequencing of pleuropulmonary blastoma reveals frequent biallelic loss of TP53 and two hits in DICER1 resulting in retention of 5p-derived miRNA hairpin loop sequences. *Oncogene,* 33 (45): p. 5295-302, 2014.

Rakheja et al., Somatic mutations in DROSHA and DICER1 impair microRNA biogenesis through distinct mechanisms in Wilms tumours. *Nat Commun,* 2: p. 4802, 2014.

Reiling, et al., The progeroid phenotype of Ku80 deficiency is dominant over DNA-PKCS deficiency. *PLOS One* 9 (4): e93568, 2014.

Swahari V, et al. (2016) Essential Function of Dicer in Resolving DNA Damage in the Rapidly Dividing Cells of the Developing and Malignant Cerebellum. *Cell Rep* 14 (2): 216-224.

Treiber et al., Accelerated aging phenotype in mice with conditional deficiency for mitochondrial superoxide dismutase in the connective tissue. *Aging Cell* 10 (2): 239-254, 2011.

What is claimed is:

1. An isolated monoclonal antibody, wherein the antibody specifically binds phosphorylated human Dicer1 (pDicer1) at Serine 1728 and/or Serine 1852, wherein the antibody specifically binds phosphorylated human Dicer1 (pDicer1) at Serine 1852 and further wherein the antibody comprises CDRs 1-3 (SEQ ID NOs: 3, 5, and 7) of the $V_H$ domain and CDRs 1-3 (SEQ ID NOs: 11, 13, and 15) of the $V_L$ domain of the antibody encoded by hybridoma clone 25.

2. The antibody of claim 1, wherein the antibody does not bind or has essentially no binding to non-phosphorylated Dicer1.

3. The antibody of claim 1, wherein the antibody comprises a $V_H$ domain at least about 80% identical to the $V_H$ domain (SEQ ID NO: 2) of clone 25 and a $V_L$ domain (SEQ ID NO: 10) at least about 80% identical to the $V_L$ domain of clone 25.

4. The antibody of claim 1, wherein the antibody comprises a $V_H$ domain identical to the $V_H$ domain (SEQ ID NO: 2) of clone 25 and a $V_L$ domain (SEQ ID NO: 10) identical to the $V_L$ domain clone 25.

5. The antibody of claim 1, wherein the antibody is recombinant.

6. The antibody of claim 1, wherein the antibody is an IgG, IgM, IgA or an antigen binding fragment thereof.

7. The antibody of claim 1, wherein the antibody is a Fab', a F(ab') 2, a F(ab') 3, a monovalent scFv, or a bivalent scFv.

8. The antibody of claim 1, wherein the antibody is a humanized antibody or de-immunized antibody.

9. The antibody of claim 1, wherein the antibody is conjugated to an imaging agent, a chemotherapeutic agent, a toxin or a radionuclide.

10. A composition comprising an antibody of claim 1 in a pharmaceutically acceptable carrier.

11. An isolated polynucleotide molecule comprising a nucleic acid sequence encoding an antibody of claim 1.

12. A recombinant polypeptide comprising an antibody $V_H$ domain comprising CDRs 1-3 (SEQ ID NOs: 3, 5, and 7) of the $V_H$ domain of clone 25 and CDRs 1-3 (SEQ ID NOs: 11, 13, and 15) of the $V_H$ domain of clone 25.

13. An isolated polynucleotide molecule comprising a nucleic acid sequence encoding a polypeptide of claim 12.

14. A host cell comprising one or more polynucleotide molecule(s) encoding an antibody of claim 1.

15. A pharmaceutical composition comprising a pDicer1 antibody of claim 1 and a pharmaceutical carrier.

16. A method for treating cancer in a subject comprising administering an effective amount of a pDicer1 antibody of claim 1 to the subject.

17. An in vitro method of detecting phosphorylated Dicer1 in a sample comprising detecting an elevated level of phosphorylated Dicer1 by measuring binding of a pDicer1 antibody of claim 1 with a sample.

* * * * *

SEQUENCE LISTING

```
<160> NUMBER OF SEQ ID NOS: 33

<210> SEQ ID NO 1
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 1

caggtccagc tgcagcagtc tgggactgtg ctggcaaggc ctggggcttc cgtgaggatg     60

tcctgtaagg cttctggcta cagctttacc agctactgga tgcactggat aaaacagagg    120

cctggacagg gtctagaatg gattggtgct atttatcctg gaaatagtgc taccaactac    180

aaccagaagt tcaagggcaa ggccaaactg actgcagtca catccgccag cactgcctac    240

atggagctca gcagcctgac aaatgaggac tctgcggtct attactgtac aagagtgggc    300

tataggtacg aagcctggtt tgcttactgg ggccaaggga ctctggtcac tgtctctgca    360


<210> SEQ ID NO 2
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 2

Val Gln Leu Gln Gln Ser Gly Thr Val Leu Ala Arg Pro Gly Ala Ser
1               5                   10                  15

Val Arg Met Ser Cys Lys Ala Ser Gly Tyr Ser Phe Thr Ser Tyr Trp
            20                  25                  30

Met His Trp Ile Lys Gln Arg Pro Gly Gln Gly Leu Glu Trp Ile Gly
        35                  40                  45

Ala Ile Tyr Pro Gly Asn Ser Ala Thr Asn Tyr Asn Gln Lys Phe Lys
    50                  55                  60

Gly Lys Ala Lys Leu Thr Ala Val Thr Ser Ala Ser Thr Ala Tyr Met
65                  70                  75                  80

Glu Leu Ser Ser Leu Thr Asn Glu Asp Ser Ala Val Tyr Tyr Cys Thr
                85                  90                  95

Arg Val Gly Tyr Arg Tyr Glu Ala Trp Phe Ala Tyr Trp Gly Gln Gly
            100                 105                 110

Thr Leu Val Thr Val Ser Ala
        115


<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Gly Tyr Ser Phe Thr Ser Tyr Trp
1               5


<210> SEQ ID NO 4
```

<211> LENGTH: 24
<212> TYPE: DNA
<213> ORGANISM: Artificial sequence
<220> FEATURE:
<223> OTHER INFORMATION: Synthetic oligo

<400> SEQUENCE: 4
ggctacagct ttaccagcta ctgg 24

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Ile Tyr Pro Gly Asn Ser Ala Thr
1 5

<210> SEQ ID NO 6
<211> LENGTH: 24
<212> TYPE: DNA
<213> ORGANISM: Artificial sequence
<220> FEATURE:
<223> OTHER INFORMATION: Synthetic oligo

<400> SEQUENCE: 6
tatttatcct ggaaatagtg ctac 24

<210> SEQ ID NO 7
<211> LENGTH: 13
<212> TYPE: PRT
<213> ORGANISM: Artificial sequence
<220> FEATURE:
<223> OTHER INFORMATION: Synthetic peptide

<400> SEQUENCE: 7

Thr Arg Val Gly Tyr Arg Tyr Glu Ala Trp Phe Ala Tyr
1 5 10

<210> SEQ ID NO 8
<211> LENGTH: 39
<212> TYPE: DNA
<213> ORGANISM: Artificial sequence
<220> FEATURE:
<223> OTHER INFORMATION: Synthetic oligo

<400> SEQUENCE: 8
acaagagtgg gctataggta cgaagcctgg tttgcttac 39

<210> SEQ ID NO 9
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 9
gacattgtgc tgacccagtc tccagcaatc atgtctgcat ctccagggga aaaggtcacc 60
atgacctgca gtgccagctc aagtgtaagt tacattcact ggtaccagca gaagtcaaac 120
acctccccca aactctggat ttatgacaca tccaaactgg cttctggagt cccaggtcgc 180
ttcagtggca gtgggtctgg aaactcttac tctctcacga tcagcagcat ggaggctgaa 240
gatgttgcca cttattactg ttttcagggg agtgggtacc cgctcacgtt cggtgctggg 300

```
accaagctgg agctgaaa                                                 318


<210> SEQ ID NO 10
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 10

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Ile
            20                  25                  30

His Trp Tyr Gln Gln Lys Ser Asn Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Leu Lys
            100                 105


<210> SEQ ID NO 11
<211> LENGTH: 5
<212> TYPE: PRT
<213> ORGANISM: Artificial sequence
<220> FEATURE:
<223> OTHER INFORMATION: Synthetic peptide

<400> SEQUENCE: 11

Ser Ser Val Ser Tyr
1               5


<210> SEQ ID NO 12
<211> LENGTH: 15
<212> TYPE: DNA
<213> ORGANISM: Artificial sequence
<220> FEATURE:
<223> OTHER INFORMATION: Synthetic oligo

<400> SEQUENCE: 12

tcaagtgtaa gttac                                                     15


<210> SEQ ID NO 13
<211> LENGTH: 3
<212> TYPE: PRT
<213> ORGANISM: Artificial sequence
<220> FEATURE:
<223> OTHER INFORMATION: Synthetic peptide

<400> SEQUENCE: 13

Asp Thr Ser
1


<210> SEQ ID NO 14
<211> LENGTH: 9
<212> TYPE: DNA
<213> ORGANISM: Artificial sequence
<220> FEATURE:
<223> OTHER INFORMATION: Synthetic oligo
```

<400> SEQUENCE: 14 gacacatcc 9

<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

Phe Gln Gly Ser Gly Tyr Pro Leu Thr
1 5

<210> SEQ ID NO 16
<211> LENGTH: 27
<212> TYPE: DNA
<213> ORGANISM: Artificial sequence
<220> FEATURE:
<223> OTHER INFORMATION: Synthetic oligo

<400> SEQUENCE: 16
tttcagggga gtgggtaccc gctcacg 27

<210> SEQ ID NO 17
<211> LENGTH: 122
<212> TYPE: DNA
<213> ORGANISM: Artificial sequence
<220> FEATURE:
<223> OTHER INFORMATION: Synthetic oligonucleotide

<400> SEQUENCE: 17
gaaattaata cgactcacta tagacccacg gcagcattct ccgttttaga gctagaaata 60
gcaagttaaa ataaggctag tccgttatca acttgaaaaa gtggcaccga gtcggtgctt 120
tt 122

<210> SEQ ID NO 18
<211> LENGTH: 21
<212> TYPE: DNA
<213> ORGANISM: Artificial sequence
<220> FEATURE:
<223> OTHER INFORMATION: Synthetic primer

<400> SEQUENCE: 18
gctcagtggc tggcatatat g 21

<210> SEQ ID NO 19
<211> LENGTH: 19
<212> TYPE: DNA
<213> ORGANISM: Artificial sequence
<220> FEATURE:
<223> OTHER INFORMATION: Synthetic primer

<400> SEQUENCE: 19
cccaactgca gctcctttg 19

<210> SEQ ID NO 20
<211> LENGTH: 21
<212> TYPE: DNA
<213> ORGANISM: Artificial sequence
<220> FEATURE:
<223> OTHER INFORMATION: Synthetic primer

<400> SEQUENCE: 20
gccgtgattt gggacaaaaa g 21

<210> SEQ ID NO 21
<211> LENGTH: 21
<212> TYPE: DNA
<213> ORGANISM: Artificial sequence
<220> FEATURE:
<223> OTHER INFORMATION: Synthetic primer

<400> SEQUENCE: 21
ccccataggt gggtttgtat c 21

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
cccccatagc tggttcaaac 20

<210> SEQ ID NO 23
<211> LENGTH: 21
<212> TYPE: DNA
<213> ORGANISM: Artificial sequence
<220> FEATURE:
<223> OTHER INFORMATION: Synthetic primer

<400> SEQUENCE: 23
ggcaacaagg gcagatacat g 21

<210> SEQ ID NO 24
<211> LENGTH: 24
<212> TYPE: DNA
<213> ORGANISM: Artificial sequence
<220> FEATURE:
<223> OTHER INFORMATION: Synthetic primer

<400> SEQUENCE: 24
cctctaggcc tgtgatcaga atag 24

<210> SEQ ID NO 25
<211> LENGTH: 22
<212> TYPE: DNA
<213> ORGANISM: Artificial sequence
<220> FEATURE:
<223> OTHER INFORMATION: Synthetic primer

<400> SEQUENCE: 25
ggcgggttaa tgactcatac ag 22

<210> SEQ ID NO 26
<211> LENGTH: 22
<212> TYPE: DNA
<213> ORGANISM: Artificial sequence
<220> FEATURE:
<223> OTHER INFORMATION: Synthetic primer

<400> SEQUENCE: 26
ggctggacat agttgtctgt tg 22

<210> SEQ ID NO 27
<211> LENGTH: 21
<212> TYPE: DNA

<213> ORGANISM: Artificial sequence
<220> FEATURE:
<223> OTHER INFORMATION: Synthetic primer

<400> SEQUENCE: 27
gctccacctg gcttcattat c 21

<210> SEQ ID NO 28
<211> LENGTH: 24
<212> TYPE: DNA
<213> ORGANISM: Artificial sequence
<220> FEATURE:
<223> OTHER INFORMATION: Synthetic primer

<400> SEQUENCE: 28
gaggaccgat ggttgtgaaa aatc 24

<210> SEQ ID NO 29
<211> LENGTH: 22
<212> TYPE: DNA
<213> ORGANISM: Artificial sequence
<220> FEATURE:
<223> OTHER INFORMATION: Synthetic primer

<400> SEQUENCE: 29
cctggcacct aggagaattt ag 22

<210> SEQ ID NO 30
<211> LENGTH: 20
<212> TYPE: DNA
<213> ORGANISM: Artificial sequence
<220> FEATURE:
<223> OTHER INFORMATION: Synthetic primer

<400> SEQUENCE: 30
gtgccaggga tgtagaagac 20

<210> SEQ ID NO 31
<211> LENGTH: 21
<212> TYPE: DNA
<213> ORGANISM: Artificial sequence
<220> FEATURE:
<223> OTHER INFORMATION: Synthetic primer

<400> SEQUENCE: 31
gggctgcagg aattcgatat c 21

<210> SEQ ID NO 32
<211> LENGTH: 23
<212> TYPE: DNA
<213> ORGANISM: Artificial sequence
<220> FEATURE:
<223> OTHER INFORMATION: Synthetic primer

<400> SEQUENCE: 32
cacgtggtac cttaagatgc atg 23

-continued

```
<210> SEQ ID NO 33
<211> LENGTH: 20
<212> TYPE: DNA
<213> ORGANISM: Artificial sequence
<220> FEATURE:
<223> OTHER INFORMATION: Synthetic primer

<400> SEQUENCE: 33

gcgggtgact tgaacctaag                                    20
```